US009903798B1

(12) United States Patent
Astle

(10) Patent No.: US 9,903,798 B1
(45) Date of Patent: *Feb. 27, 2018

(54) DRIED SPECIMEN STORAGE SLIDES, SYSTEMS AND METHODS

(71) Applicant: Thomas W. Astle, Orange, CT (US)

(72) Inventor: Thomas W. Astle, Orange, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/337,164

(22) Filed: Oct. 28, 2016

Related U.S. Application Data

(63) Continuation of application No. 14/665,219, filed on Mar. 23, 2015, now Pat. No. 9,546,935, which is a
(Continued)

(51) Int. Cl.
*G01N 1/31* (2006.01)
*G01N 35/00* (2006.01)
(Continued)

(52) U.S. Cl.
CPC ....... *G01N 1/312* (2013.01); *G01N 35/00029* (2013.01); *B01L 3/5025* (2013.01);
(Continued)

(58) Field of Classification Search
CPC ............. B01L 2300/0829; B01L 9/523; B01L 3/5085; B01L 2300/044; B01L 3/50853;
(Continued)

(56) References Cited

U.S. PATENT DOCUMENTS 4,668,472 A 5/1987 Sakamoto et al.
4,789,629 A 12/1988 Baker et al.
(Continued)

FOREIGN PATENT DOCUMENTS

EP 1056336 12/2000
WO 0112783 2/2001

OTHER PUBLICATIONS

Efficiency of Hyaluronic Acid (HA) Sperm Selection, Journal of Assisted Reproduction and Genetics, Jan. 2010, vol. 27, Issue 1, pp. 13-16.
(Continued)

*Primary Examiner* — Lyle Alexander
*Assistant Examiner* — Bryan T Kilpatrick
(74) *Attorney, Agent, or Firm* — DeLio, Peterson & Curcio LLC; Kelly M. Nowak

(57) ABSTRACT

Specimen collection slides, methods of fabricating and methods of utilizing such specimen collection slides whereby each specimen collection slide includes a top rigid layer with an opening, a bottom rigid layer with an opening substantially the same size as the top layer opening, a middle rigid section having an opening larger than the openings in both the top and bottom layers, and a filtration media residing within the opening in the middle section. The top, bottom and middle are secured together to provide the resultant slide with thickness and rigidity that lends the slide to be utilized in automated handling processes and instruments. The middle section of the slide encases the filtration media and sandwiches it between the top and bottom layers so that the filtration media is protected from damage. Each slide may have its own unique identifier.

18 Claims, 20 Drawing Sheets

Related U.S. Application Data continuation of application No. 12/868,229, filed on Aug. 25, 2010, now Pat. No. 9,575,084, and a continuation of application No. 13/462,025, filed on May 2, 2012, now Pat. No. 9,150,983.

(51) Int. Cl.

| | | |
|---|---|---|
| G01N 1/28 | (2006.01) | |
| G01N 35/10 | (2006.01) | |
| G01N 21/64 | (2006.01) | |
| B01L 3/00 | (2006.01) | |
| B01L 9/00 | (2006.01) | |

(52) U.S. Cl.
CPC .......... *B01L 3/5085* (2013.01); *B01L 3/50853* (2013.01); *B01L 9/52* (2013.01); *B01L 9/523* (2013.01); *B01L 2200/141* (2013.01); *B01L 2200/18* (2013.01); *B01L 2300/021* (2013.01); *B01L 2300/0822* (2013.01); *G01N 21/6452* (2013.01); *G01N 2001/288* (2013.01)

(58) Field of Classification Search
CPC .......... B01L 3/5025; B01L 3/527; B01L 9/52; G01N 35/1065; G01N 1/312; G01N 2001/288; G01N 21/6452; Y10T 436/2575; Y10T 436/255; C12Q 1/24
See application file for complete search history.

(56) References Cited

U.S. PATENT DOCUMENTS

| | | | |
|---|---|---|---|
| 4,948,442 A | 8/1990 | Manns | |
| 5,139,031 A | 8/1992 | Guirguis | |
| 5,139,685 A | 8/1992 | de Castro et al. | |
| 5,460,057 A * | 10/1995 | Ostrup | B01L 3/545 422/65 |
| 5,516,487 A * | 5/1996 | Rosenthal | G01N 33/521 422/420 |
| 5,597,532 A | 1/1997 | Connolly | |
| 5,665,238 A * | 9/1997 | Whitson | B01L 3/5023 210/483 |
| 6,129,214 A | 10/2000 | Bar-Ami et al. | |
| 6,818,180 B2 | 11/2004 | Douglas et al. | |
| 7,838,509 B2 | 11/2010 | Ellington et al. | |
| 8,025,850 B2 | 9/2011 | Chan | |
| 8,586,382 B2 | 11/2013 | Gijlers et al. | |
| 9,546,935 B1 * | 1/2017 | Astle | G01N 1/312 |
| 9,575,084 B1 * | 2/2017 | Astle | G01N 35/0098 |
| 2007/0202542 A1 | 8/2007 | Babu et al. | |

OTHER PUBLICATIONS

Efficacy of Hyaluronic Acid Binding Assay in Selecting Motile Spermatozoa With Normal Morphology at High Magnification, Claudia G. Petersen et al., Reproductive Biology and Endocrinology 2010, 8:149; http://www.rbej.com/content/8/1/149.

\* cited by examiner

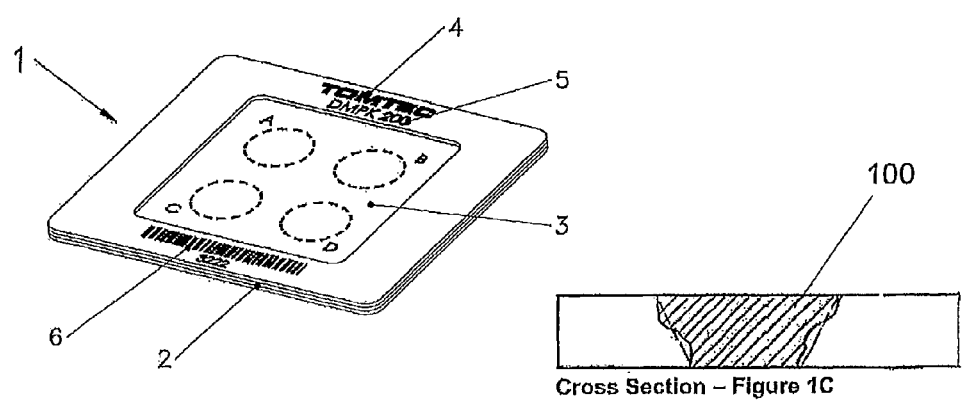
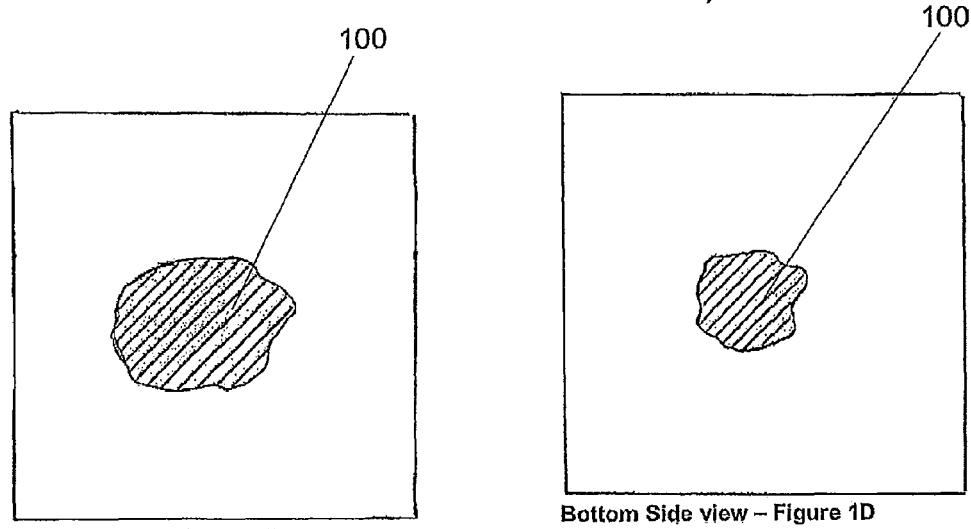
FIG. 7A
FIG. 7C
FIG. 7B
FIG. 7D

Calculated Volumes of spots in mm³

| Hematocrit Level | DMPK 200 ||||||
|---|---|---|---|---|---|---|
| | Pipettor Volume ||| Aqua Cap Volume |||
| | 15uL | 25uL | 40uL | 15uL | 25uL | 40uL |
| 25% | 19.36 | 32.47 | 52.22 | 21.75 | 34.68 | 53.56 |
| 35% | 19.07 | 32.66 | 51.39 | 21.10 | 33.40 | 52.15 |
| 45% | 18.58 | 29.79 | 47.32 | 19.58 | 31.78 | 49.45 |
| 55% | 18.01 | 29.76 | 45.87 | 19.37 | 31.31 | 47.60 |
| 65% | 17.51 | 27.47 | 41.50 | 18.57 | 29.35 | 43.82 |
| 75% | 15.59 | 23.95 | 35.82 | 16.70 | 27.01 | 37.76 |

| Hematocrit Level | DMPK 300 ||||||
|---|---|---|---|---|---|---|
| | Pipettor Volume ||| Aqua Cap Volume |||
| | 15uL | 25uL | 40uL | 15uL | 25uL | 40uL |
| 25% | 25.65 | 41.22 | 65.23 | 26.78 | 42.06 | 65.56 |
| 35% | 23.25 | 37.93 | 58.47 | 24.67 | 38.54 | 60.75 |
| 45% | 19.11 | 30.98 | 48.47 | 20.33 | 32.72 | 50.40 |
| 55% | 19.16 | 29.67 | 45.37 | 20.09 | 32.13 | 47.92 |
| 65% | 17.27 | 28.10 | 43.35 | 19.21 | 30.44 | 46.10 |
| 75% | 16.78 | 25.95 | 40.68 | 18.13 | 29.78 | 43.49 |

| Hematocrit Level | DMPK 400 ||||||
|---|---|---|---|---|---|---|
| | Pipettor Volume ||| Aqua Cap Volume |||
| | 15uL | 25uL | 40uL | 15uL | 25uL | 40uL |
| 25% | 24.74 | 39.41 | 61.67 | 25.11 | 40.61 | 63.07 |
| 35% | 22.20 | 35.87 | 56.26 | 23.00 | 36.51 | 57.98 |
| 45% | 18.79 | 30.93 | 48.77 | 20.22 | 32.74 | 50.53 |
| 55% | 18.84 | 30.30 | 46.29 | 19.99 | 31.71 | 48.13 |
| 65% | 17.06 | 28.33 | 43.53 | 18.93 | 30.38 | 46.47 |
| 75% | 17.63 | 26.92 | 41.52 | 18.11 | 30.07 | 44.27 |

FIG. 20

DRIED SPECIMEN STORAGE SLIDES, SYSTEMS AND METHODS

This application is a continuation application of pending application Ser. No. 14/665,219 filed Mar. 23, 2015, which is a continuation application of Ser. No. 12/868,229 filed Aug. 25, 2010 and Ser. No. 13/462,025 filed May 2, 2012, all of which are hereby incorporated by reference in their entireties.

BACKGROUND OF THE INVENTION

1. Field of the Invention

The present invention is directed to specimen storage slides, and in particular, to methods of use and specimen storage slides for the transportation and storage of dried specimens.

2. Description of Related Art

In 1963 Guthrie developed a method for collecting blood samples on absorbent filtration media. The blood samples were dried and transported to the laboratory for analysis. Today, dried blood spots (DBS) are used for mandatory newborn screening programs in the U.S. and in many other nations worldwide. DBS methods have also become common in other medical and forensic applications.

With the advancement of analyte detection methods, primarily liquid chromatography combined with mass spectroscopy (LC-MS or LC-MS/MS), interest has been expanded for the use of DBS for preclinical and clinical applications in lieu of plasma. The small blood volumes required, and the lower transportation and storage costs, are the driving factors. For preclinical applications, there is a significant reduction in the number of-animals that are sacrificed, contributing to the ethics of DBS. Dried blood spots are also stable for an extended period of time, often measured in years if the DBS is kept dry. This eliminates the cold storage and shipping requirement needs of plasma, which will drastically reduce costs.

A change from plasma to DBS creates many new challenges to meet the requirements of public health. For the last two years, extensive method development for DBS has occurred in the Bioanalytical market to meet the requirements that are being defined by the U.S. Food and Drug Administration (hereinafter "FDA") for meeting public health safety standards. The FDA, as the guardian of public health, will accept DBS studies only after they have met or exceeded predefined health standards that have been established for plasma.

A variety of fields implement the use of cards to store dried specimens. These specimens may include chemical samples, biological samples, and the like. For instance, dried blood spots stored on paper cards have been in use for years in a variety of fields ranging from clinical, preclinical, research, forensics, and the like. More recently there has been an increase in the use of dried blood spots in clinical applications, such as, in neo-natal screening, DNA analysis, disease analyses (infectious disease, blood glucose concentration, etc.), drug screenings, and the like. Preclinical applications for dried blood spots, such as, medical research, drug discoveries, and the like, are also becoming more prevalent.

In the collection of dried blood spots, a number of drops of obtained blood are deposited in predetermined locations on filter paper of a paper collection card. These collection cards include an absorbent filter paper that is encased within a cardboard frame, attached inside a cardboard card, or attached to a paper sheet. The collection cards may also be provided with a source for sample identification, such as, a demographic portion where information about the sample and the submitter's identification can be entered. The blood specimen is allowed to dry on the collection card for storage, transportation and/or later use thereof.

However, a detriment of the currently available specimen collection cards is that since they are composed of either paper sheets or cardboard these conventional collection cards are flimsy and easily damaged. Also, in collection cards having a paper or cardboard frame encasing the filter paper media, the frame is typically not much thicker than the filter paper media it encases. As such, when one or more of these types of cards are stacked upon one another, their respective filter paper medias contact each other causing sample cross contamination, which is highly undesirable. Accordingly, it is often necessary to store each framed paper or cardboard collection card in an envelope separate from one another.

Furthermore, both current and future clinical and preclinical application systems or equipment are leaning towards automated handling, automated processing, and/or automated sample collection. Currently available paper and/or cardboard collection cards are inadequate for automated handling, processing, and/or sample collection due to their flimsiness or lack of dimensional stability. Rather, these conventional cards must be individually hand picked and placed into or onto the automated systems and equipment to prevent damage thereto, which in turn, leads to slower processing times and more costly analyses.

Accordingly, a need exists in the art for improved specimen collection storage devices that are durable, easily useable, are structurally and mechanically stable, have sufficiently rigidity for handling and processing, avoid specimen cross contamination, are adapted for automated handling, automated processing, and/or automated sample collection, and allow for faster processing times and reduced costs.

SUMMARY OF THE INVENTION

Bearing in mind the problems and deficiencies of the prior art, it is therefore an object of the present invention to provide specimen collection slides that are durable and both structurally and mechanically stable.

It is another object of the present invention to provide specimen collection slides having sufficiently rigidity for manual and/or mechanically automated handling and processing.

A further object of the invention is to provide specimen collection slides that prevent cross contamination of specimens residing on adjacent slides.

Another object of the present invention is to provide specimen collection slides that are easily useable, cost effective and allow for faster processing times.

It is yet another object of the present invention to provide methods of making and implementing the various specimen collection slides in accordance with the various embodiments of the invention.

Another object of the present invention is to provide systems that easily, efficiently and accurately obtain samples from a filtration media slide for analysis.

It is another object of the present invention to provide methods for easily, efficiently and accurately obtaining samplings or portions of dried specimens stored on a filtration media slide for analysis.

Another object of the present invention is to systems and methods for easily, efficiently and accurately obtaining dried blood spots from media slides for analysis.

It is yet another object of the present invention to provide systems and methods of obtaining specimen samples (e.g., dried blood spot samples) that are cost effective and allow for faster processing times.

Still other objects and advantages of the invention will in part be obvious and will in part be apparent from the specification.

The above and other objects, which will be apparent to those skilled in the art, are achieved in the present invention which is directed to a specimen collection slide that includes a first layer of a first non-fibrous material having a first central opening; a second layer of a second non-fibrous material having a second central opening attached to the first layer, the first and second central openings being in alignment with each other; and a filtration media layer for retaining a sample residing between the first and second layers, the filtration media being accessible through both the first and second central openings whereby together the first and second layers provide the specimen collection slide with a thickness sufficient for handling.

In other embodiments the invention is directed to a specimen collection slide that includes a first rigid layer having a first central opening; a second rigid layer having a second central opening larger than the first central opening; a filtration media layer for retaining a sample residing entirely within the second central opening of the second rigid layer, the second rigid layer protecting the filtration media from damage thereto; and a third rigid layer having a third central opening substantially the same size as the first central opening. The first, second and third rigid layers have substantially identical external dimensions, and are securely attached together without damaging the filtration media to provide the specimen collection slide with a thickness sufficient for handling.

In still other embodiments the invention is directed to one or more methods of fabricating a specimen collection slide that includes providing a first rigid layer having a first central opening; providing a second rigid layer having a second central opening larger than the first central opening; positioning a filtration media layer entirely within the second central opening of the second rigid layer to protect the filtration media; providing a third rigid layer having a third central opening substantially the same size as the first central opening; aligning the first, second and third rigid layers so that the second rigid layer and the filtration media layer reside between the first and third rigid layers; and securing the first, second and third rigid layers together without damaging the filtration media.

In these embodiments, the specimen collection slide may have a total thickness sufficient for automatic handling. The methods may further include pre-treating the filtration media layer with an internal standard. The first, second and third rigid layers may comprise an identical material. The first, second and third rigid layers may comprise a plastic material. The first, second and third rigid layers may be bonded or ultrasonically welded together.

The invention is still further directed to a method of utilizing a specimen collection slide comprising providing a specimen collection slide that includes a top rigid layer with a first central opening, a bottom rigid layer having a second central opening substantially the same size as the first central opening, a middle rigid layer having a third central opening larger than both the first and second central openings, a filtration media layer having one or more delineated sample locations defining locations where a sample is to be deposited thereon residing entirely within the central opening of the middle rigid layer, both the filtration media and the middle rigid layer residing between the top and bottom rigid layers, whereby the top, middle and bottom rigid layers are securely attached together. The methods proceed with obtaining at least one sample specimen from at least one source; accessing the filtration media layer through one of the first or second central openings; depositing the at least one sample specimen onto the filtration media at the one or more delineated sample locations; absorbing the at least one sample specimen into the filtration media; and allowing the deposited at least one sample specimen to dry on the filtration media for a subsequent analytical testing procedure.

When the specimen collection slide is a first specimen collection slide having a first filtration media layer with one or more dried specimens thereon, the methods may further include providing a second specimen collection slide having a second filtration media layer with one or more other dried specimens thereon; and providing the second specimen collection slide over the first specimen collection slide such that the top rigid layer of the first specimen collection slide contacts the bottom rigid layer of the second specimen collection slide, whereby a thickness of the top rigid layer of the first specimen collection slide and a thickness of the bottom rigid layer of the second specimen collection slide together provide a distance between the first filtration media layer and the second filtration media layer that prevents contact between the adjacent filtration media layers and prevents cross-contamination of any samples residing on the adjacent filtration media layers.

Still other objects and advantages of the invention are achieved in the present invention which is directed to apparatus for processing a specimen collection slide. The apparatus includes a slide transport component for receiving and holding a sample slide containing an absorbed specimen, and first and second imaging stations. The first imaging station has a first lighting assembly and a first camera that images a first surface of the sample slide. The first camera is adjacent to and directed at the first surface of the sample slide and the first lighting assembly is directed at an opposite second surface of the sample slide for capturing the first surface image. The second imaging station has a second lighting assembly and a second camera that images the second surface of the sample slide. The second camera is adjacent to and directed at the second surface of the sample slide and the second lighting assembly is directed at the first surface of the sample slide for capturing the second surface image. The apparatus also includes a computing device and a punch. The computing device receives imaging data from the first and second imaging stations and includes a set of instructions that analyze the imaging data and identify a location of the absorbed specimen for removal. The punch removes this identified location of the absorbed specimen on the sample slide.

The invention is also directed to methods of processing a specimen collection slide that include providing a sample slide containing a specimen absorbed through a thickness thereof, and transporting such slide into a processing tool having first and second imaging stations. A first surface of the sample slide is imaged by providing the sample slide in the first imaging station whereby a first lighting assembly illuminates a second surface of the sample slide while a first camera captures a first image of the absorbed specimen on the first surface of the sample slide. A second surface of the sample slide is imaged by providing the sample slide in the second imaging station whereby a second lighting assembly illuminates the second surface of the sample slide while a second camera captures a second image of the absorbed specimen on the second surface of the sample slide. Data of the first and second captured images is transmitted to a computing device having a set of instructions, and using this set of instructions, data of the first and second captured images is analyzed to determine and identify a location of the absorbed specimen for removal. The identified location of the absorbed specimen on the slide is then removed for subsequent processing.

The methods may also further include analyzing and comparing the first image of the absorbed specimen on the first surface against the second image of the absorbed specimen on the second surface to determine a flow pattern of the absorbed specimen through the sample slide. In doing so, the saturation volume area may be calculated using at least the differential between the first image and the second image in combination with a thickness measurement of the sample slide. In one or more embodiments, the invention includes a sample slide containing a specimen includes permanent laser markings that at least uniquely identify the specimen on the sample slide.

The invention is still further directed to a method of utilizing a specimen collection slide comprising providing a specimen collection slide that includes a top rigid layer with a first central opening, a bottom rigid layer having a second central opening substantially the same size as the first central opening, a middle rigid layer having a third central opening larger than both the first and second central openings, a filtration media layer having one or more delineated sample locations defining locations where a sample is to be deposited thereon residing entirely within the central opening of the middle rigid layer, both the filtration media and the middle rigid layer residing between the top and bottom rigid layers, whereby the top, middle and bottom rigid layers are securely attached together. The methods proceed with obtaining at least one sample specimen from at least one source; accessing the filtration media layer through one of the first or second central openings; depositing the at least one sample specimen onto the filtration media at the one or more delineated sample locations; absorbing the at least one sample specimen into the filtration media; and allowing the deposited at least one sample specimen to dry on the filtration media for a subsequent analytical testing procedure.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 7A is a perspective view of a filtration media slide suitable for use in the present invention.

FIG. 7B is a top view of the front side of a slide having a fluid sample deposited on the filtration media.

FIG. 7C is a cross sectional view of a slide showing the flow pattern of the deposited fluid sample traversing through a thickness of the filtration media.

FIG. 7D is a bottom view of the backside of a slide having the deposited fluid sample.

FIG. 20 are charted test data results of imaged front side DBS slides showing the spread patterns of low hematocrit blood samples as compared to high hematocrit blood samples.

DESCRIPTION OF THE PREFERRED EMBODIMENT(S)

Figure 1A:
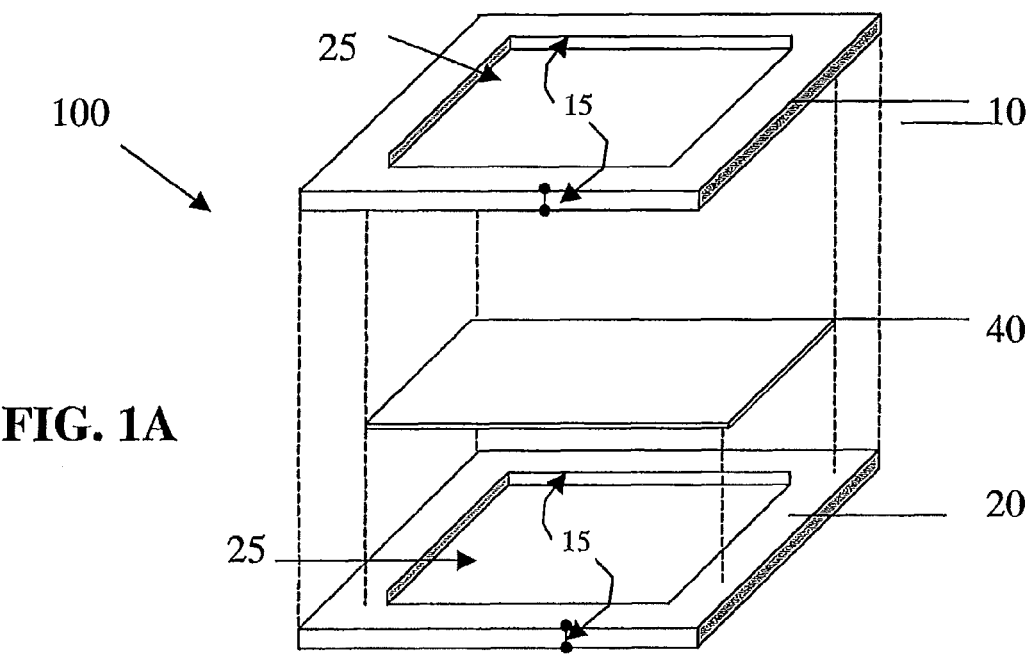
FIG. 1A is a perspective view showing components of a specimen collection slide according to one or more embodiments of the present invention.

In describing the preferred embodiment of the present invention, reference will be made herein to FIGS. 1A-22 of the drawings in which like numerals refer to like features of the invention.

Terms such as "above", "below", "upper", "lower", "inner", "outer", inwardly", "outwardly", "vertical", "horizontal", and the like, when used herein, refer to the positions of the respective elements shown on the accompanying drawing figures and the present invention is not necessarily limited to such positions. In the embodiments of the present invention described herein, it will be recognized that individual elements and/or features thereof are not necessarily limited to a particular embodiment but, where applicable, are interchangeable and can be used in any selected embodiment even though such may not be specifically shown.

The present invention is directed to specimen collection slides, systems and methods of use thereof. The various specimen collection slides of the invention are durable, structurally and mechanically stable, and have sufficient rigidity for handling and processing in automated systems and/or equipment. With the increasing use of specimen collection slides in both preclinical and clinical applications, the one or more embodiments of the invention allow for easy and efficient automated handling, automated processing, and/or automated sample collection using the specimen collection slides of the invention. The configurations of the present specimen collection slides also prevent cross contamination of specimens residing on adjacent collection slides both during the use and storage of such slides.

In accordance with the various embodiments, the specimen collection slides of the invention may be used in both preclinical applications and clinical applications. Preclinical applications may include, but are not limited to, the development and discovery of drugs, their analytes and drug assays; disease discovery and detection tests; research and development of analytical testing in a variety of scientific fields and environments, and the like. Clinical applications may include, but are not limited to, DNA analysis; Neo-Natal screening; disease detection and diagnosis; drug, chemical or analyte testing and detection, and the like. While the foregoing uses are not meant to limit the scope of the invention, many additional uses of the present specimen collection slides exist and will be appreciated and understood in accordance with the description of the invention.

Since the present specimen collection slides are suitable for use with various applications, the specimens collected on such slides may also vary depending upon the end use of each collection slide. The specimen collected on the collection slides of the invention may be one or more purely biological samples, one or more purely chemical samples, or the specimens may be a combination of one or more biological and chemical samples. For instance, a purely biological sample may include, but is not limited to, blood, saliva, bodily secretions, organic matter, and the like. A purely chemical sample may include, but is not limited to, a drug, an analyte, an organic or inorganic chemical compound, and the like. A sample that includes both biological and chemical components, may include, but is not limited to, a blood sample being tested for presence of a drug, bodily secretions being tested for presence of an organic or inorganic chemical compound, such as, a contaminant (e.g., a poison), and the like.

While not meant to limit the invention, in one or more embodiments the present collection slides may be used to collect one or more dried blood spots. Dried blood spots (DBS) are used to transport a blood specimen from a source to the point of analysis. In so doing, small volumes of blood may be obtained from a source which may include, but is not limited to, an individual, patient, newborn, crime scene, laboratory sample, laboratory test animal, and the like. For instance, the blood sample may be obtained by a finger or heel stick of an individual. The amount of blood required for depositing on a single specimen collection slide may range from less than or equal to about 15 μL to greater than or equal to about 50 μL. One or more drops of the collected blood sample is/are deposited onto predefined location(s) on the filter paper media of the specimen collection slide, and allowed to dry. A typical drying time may range from less than or equal to about 2 hours to greater than or equal to about 3 hours. Once dried, the dried blood spots are stable on the present collection slides for 2-5 years, or even more.

In the specific application of using dried blood spots for clinical and/or preclinical applications, the analyte may be analyzed using liquid chromatography combined with mass spectroscopy (LC-MS or LC-MS/MS). For this type of application, the use of an internal standard is preferably included on a surface of the filtration media of the present collection slides, or throughout an entire thickness of such filtration media.

The use of an internal standard serves to normalize system response(s). In conventional approaches internal standard is mixed at a constant concentration with the nominal aliquot volume of sample. From that point on, errors in handling are compensated for by evaluating the response ratio of analyte to internal standard. For instance, if a transfer is made of a different volume of the sample mixture post internal standard addition, the ratio will provide a correction factor. The change in the internal standard response would indicate the difference in processing.

In Mass Spectrometer (MS) detection the need for internal standard is often critical since the MS monitors only the analyte mass transition while the effects of other interferences are not detectable from one sample to the next. Examples include dosing formulations of endogenous compounds that vary in their amount from sample to sample. These unseen components may suppress ionization of the analyte. By having an internal standard that coelutes with the analyte and is structurally similar, variations in ion suppression are factored out.

In clinical programs the internal standard is typically a stable labeled version of the analyte with deuterium substituted in hydrogen positions (Mass 1 replaced with Mass 2) and/or heavy carbon atoms (carbon 13 replacing carbon with 12 mass units) incorporated to give a different mass. Yet, the structure is identical with the analyte and so it coelutes and ionizes such analyte. For example, in a case where there are high levels of dosing vehicle PEG present in the first couple of time-points of a pharmacokinetic study, it may suppress the ionization by 80%. It does this both for the analyte and the stable labeled internal standard. The ratio of analyte to internal standard response remains the same, despite the 80% reduction in absolute response. This can still be compared with the standard curve response ratios, even though there is no suppression going on with the standards.

Again, in conventional approaches internal standard is added to the sample itself that is to be analyzed. In instances where the addition of internal standard is made at the point of use (i.e., added to the sample itself), a variety of methods may be implemented, depending on the choice and methods chosen by each individual end-user or laboratory. However, this can undesirably lead to inconsistencies when comparing results between different test or sample runs, or even between different laboratories involved in conducting a combined clinical study.

In accordance with the various embodiments of the invention, in order to avoid the inconsistencies in results of the conventional approaches of adding internal standard, the internal standard is added to the present specimen collection slides at the point of manufacturing such slides. That is, the internal standard of choice, for a specific project, is included on a surface of, or throughout an entire thickness of, the filtration media of the present collection slides at the point of manufacturing such slides.

At the point of manufacturing, a more precise method of adding the internal standard directly to the slides themselves may be implemented for all of the present collection slides, which may be used to support a specific clinical study. Again, with the use of dried blood spots for clinical and preclinical applications both the analyte and the internal standard on the slide may be stable for a number of years (e.g., for the life of the study or trial). By adding a preselected or desired internal standard directly onto or within the specimen collection slides of the invention (i.e., onto or within the filtration media of such slides) at the point of manufacture, the present specimen collection slides provide an improved degree of statistical control over the parameters involved and the credibility of performance of the end result.

In the one or more embodiments of the invention, the present specimen collection slides are at least composed of filtration media and a structural support for the filtration media. The filtration media is preferably capable of absorbing and retaining a liquid phase sample, which is applied and soaked into the fibers of the media and allowed to thy thereon and therein. The filtration media may be derived from several sources including, but not limited to, natural fibers, such as, wood fibers, cotton fibers, and the like. In one or more embodiments, wood fibers are preferred, while in other embodiments cotton linters are preferred, particularly for clinical and preclinical applications.

The structural support of the present specimen collection slides not only provide support for the filtration media retained therein, it also enables the easy and efficient implementation of the present slides with automated handling and processing systems. The structural support component of the present slides also provide protection against physical contact of the sample that is contained on the filtration media. Since the filtration media has samples on both sides, due to the soaking action, both sides of the filter media should be protected against intimate and direct contact with other or adjacent filter media also containing samples. In so doing, the filtration media of the present slides is sandwiched between at least two layers or pieces of structural support material.

The structural support material may be any material that provides rigidity for support, handling and integrity of the resultant slide, which is preferably easy to handle and preferably low cost. For instance, in one or more embodiments the structural support material may be a thermoplastic polymer, such as, polystyrene sheet stock, cut to size of the desired resultant slide. Polystyrene sheet stock is available in a variety of thicknesses and may be cut by shearing or die cutting. In other embodiments, the structural support may be made by injection molding using a material having sufficient rigidity upon completion of the final slide.

Figure 1B:
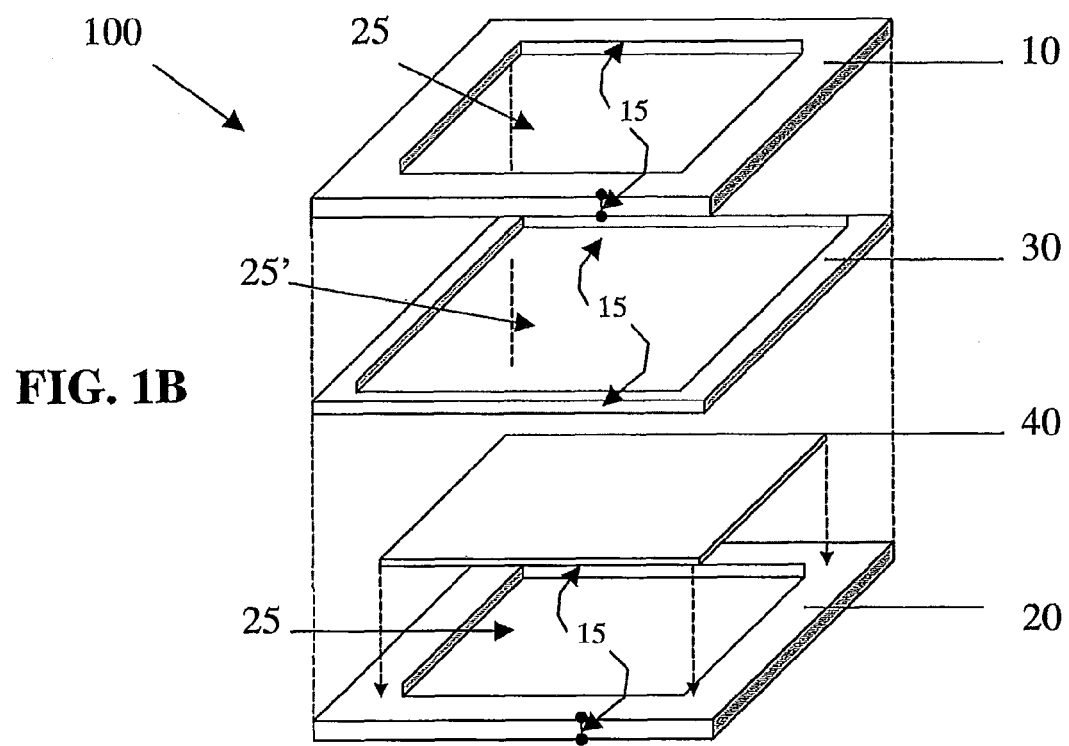
FIG. 1B is a perspective view showing components of a specimen collection slide according to one or more alternate embodiments of the invention.

For ease of understanding the invention, reference will now be made to the drawings wherein like numerals refer to like features of the invention. Referring to FIGS. 1A-B, the specimen collection slides 1 of the various embodiments of the invention at least include a pair of rigid frames 10, 20 with a sheet of filtration media 40 residing securely between the frames 10, 20. The filtration media 40 is encased between the first frame 10 and second frame 20. As is shown in FIG. 1B, in those embodiments wherein the rigid frames are cut or machined from a rigid sheet of material a third rigid frame 30 may reside between the first rigid frame 10 and the second rigid frame 20. This third rigid frame 30 also assists in holding and securing the filtration media 40 between the outer rigid frames 10, 20, as well as provides additional rigidity for assembly of the resultant slide.

Figure 1C:
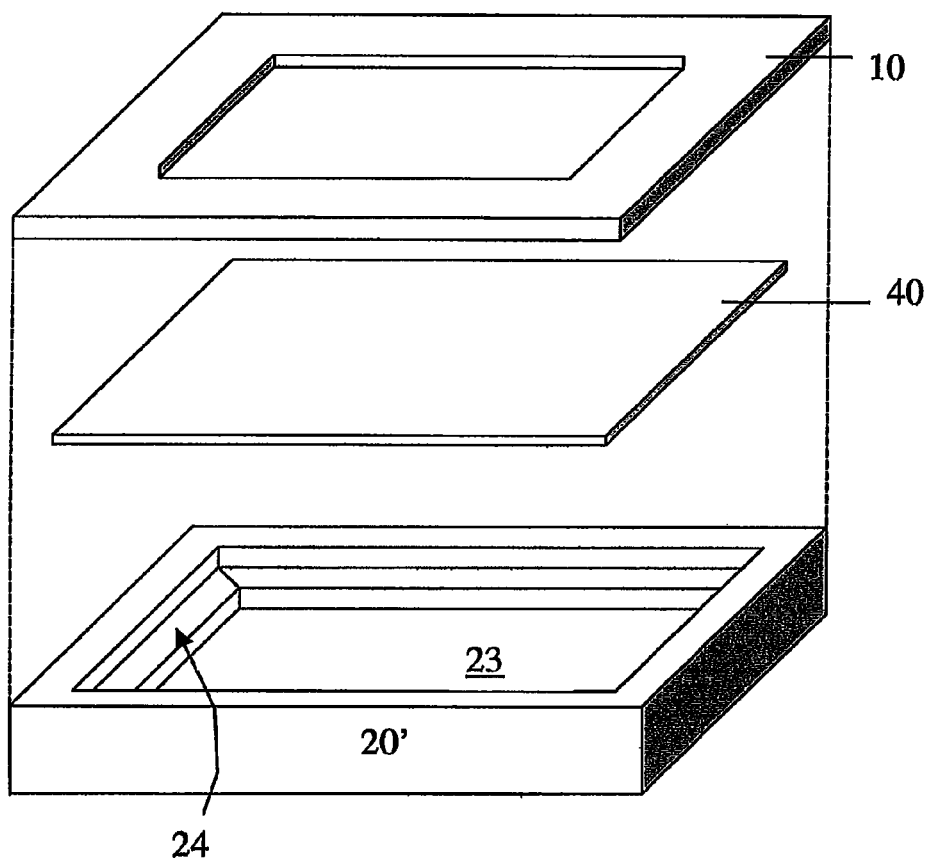
FIGS. 1 C-D are perspective views showing components of a specimen collection slide according to still other embodiments of the invention.
Figure 1D:
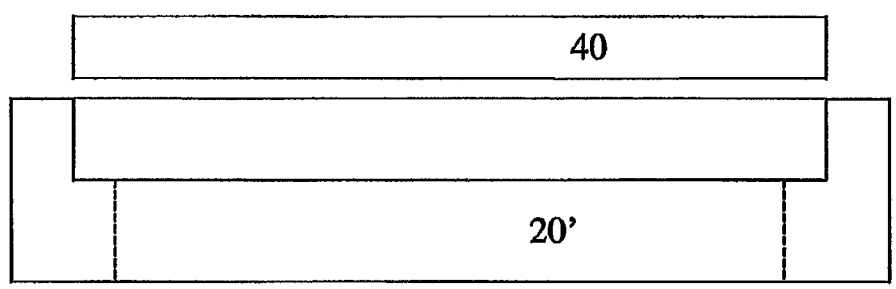

As is shown in FIGS. 1C-D, in other embodiments wherein the structural support is fabricated using injection molding techniques, the outer frame 20' may be fabricated as a single piece having an opening 23 adapted to receive and retain the filtration media 40 therein. This opening 23 preferably includes a ledge or lip area 24 capable of receiving and holding the filtration media inside the outer frame 20', such that, when the filtration media is residing therein, the filtration media and a top surface of the outer frame 20' are substantially planar with one another. The other outer frame 10 is similar to that described in relation to FIGS. 1A and 1B.

In all embodiments, the rigid frames (e.g., outer rigid frames 10, 20; or outer rigid frames 10, 30, 20; or outer rigid frames 10, 20') are all composed of a material having sufficient rigidity so as to prevent damage to the final specimen collection slide 1 (e.g., to prevent bending of such resultant slide). In those preferred embodiments including a third rigid frame 30, this third rigid frame 30 is also of a sufficiently rigid material that helps to prevent damage to the slide 1 and the sheet of filtration media 40 residing therein.

In accordance with the invention each frame 10, 20, 30 is provided with a sufficient thickness 15 both on its external edges and at edges inside its respective central opening 25. The thickness 15 of the frames 10, 20, 30 provide each frame with sufficient rigidity to prevent damage thereto, as well as to prevent damage to the overall resultant slide 1 when the frames are secured, bonded or welded together. The rigidity and thickness of each frame, and as such the overall resultant slide, also provides for ease of handling the slides as well as for ease of use and automation of each slide.

In one or more embodiments wherein the frames are fabricated by shearing or cutting, the material of the rigid frames 10, 20, and/or 30 may be a plastic material, such as, a thermoplastic polymer (e.g., polystyrene). For instance, the frames 10, 20, and/or 30 may be a polystyrene material of a high impact polystyrene sheet stock of mill rolls, whereby each rigid frame 10, 20, 30 is cut from the mill roll into predetermined dimensions as required to meet the desired dimensions of the final specimen collection slide 1. Each rigid frame may be cut from the mill roll in a controlled manner using a punch and die set, whereby repeatable dimensions of the cut frames 10, 20, 30 are preferably held to tolerances on the order of ±0.010 inches. Holding the repeatable dimensions to such standards is desirable to ensure reliable automated handling of the finished specimen collection slides 1 of the invention.

As shown in FIGS. 1A-B, the first 10, second 20 and third 30 rigid frames are all provided with a central opening 25 or window substantially at a middle of each frame. The first 10, second 20 and third 30 rigid frames also all have the same external dimensions of length and width. For purposes of illustrating the invention, in one or more embodiments the first 10, second 20 and third 30 rigid frames each may be composed of a high impact approximately 0.030 inch thick plastic material, such as, a thermoplastic polymer (e.g., polystyrene). The outer dimensions of each frame may be about 2.750 inches in length by about 2.500 inches in width, with the central opening 25 in each of the outer frames 10, 20 measuring about 1.750 inches by about 1.750 inches substantially in the middle of each frame to provide access to the filtration media sandwiched there-between.

The central opening 25 of each of the first (i.e., top) frame 10 and the second (i.e., bottom) frame 20 have substantially the same dimensions and provide access to the filtration media 40. However, the central opening 25' of the third rigid frame 30 is preferably sized to be larger than the openings in both the top and bottom frames 10, 20, as well as being slightly larger than the external dimension of the filtration media 40. That is, the external dimensions of the filtration media 40 exceed the dimensions of the access windows or openings 25 in each of the top and bottom frames 10, 20; however, are smaller than the external dimensions of such top and bottom frames 10, 20. As such, the third rigid frame 30 forms a cavity between the top and bottom frames 10, 20 to trap or capture the filtration media 40 without crushing any fibers thereof. Crushing of the filtration media fibers is undesirable since any crushing of fibers alters the density thereof, and as such, affects its ability to absorb liquid, which may be deleterious for end results of some applications.

In accordance with one or more preferred embodiments of the invention, by providing the third (i.e., middle) frame 30 with a thickness 15 that is greater than the thickness of the filter media 40 (which is retained and physically trapped by and within such frame 30), crushing of any fibers of such filter media is thereby prevented. If the filtration media has a greater thickness than the third member, then the amount of crushing is reduced by the difference in the relative thickness. As an alternative, a different thickness of material may be used for the third member 30.

Figure 4A:
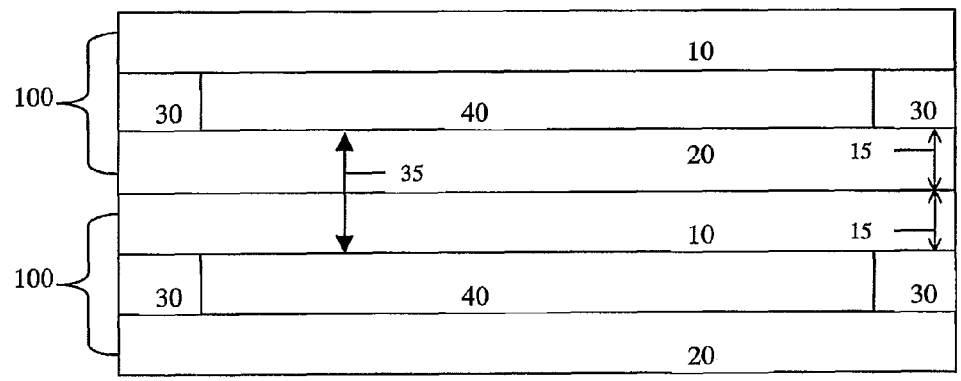
FIG. 4A shows a cross sectional view of the resultant specimen collection slide of FIG. 3A along line A-A'.
Figure 4B:
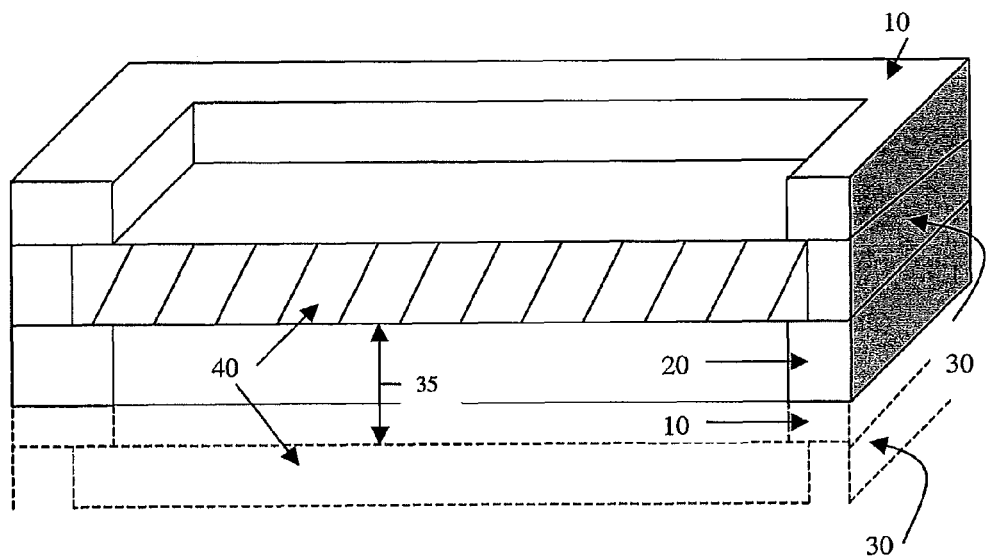
FIG. 4B shows a cross sectional view of a first slide 1 and a partial second slide of FIG. 4A showing the distance between adjacent sheets of filtration media.

Referring to the cross sectional views of FIGS. 4A-B along lines A-A' and B-B', respectively, the thickness 15 of each frame also provides each specimen collection slide 1 with the advantage that the filtration media 40 of adjacent slides 1 do not contact each other when two or more slides 1 are stacked one on top of the other. That is, when a first slide 1 is stacked upon a second slide 1, an empty cavity 38 is formed between exposed adjacent sheets of media. This empty cavity 38 has a thickness 35 approximately equal to the combined thicknesses 15 of a frame 10 of the first slide and a frame 20 of the second slide (minus any thickness of the sheet of filtration media that may be extending into the empty cavity 38). The empty cavity prevents the exposed adjacent sheets of filtration media 40 from contacting each other. This non-contact between adjacent sheets of filtration media 40 avoids cross contamination between specimens residing on these adjacent sheets of filtration media.

Unlike conventional paper or cardboard collection cards that are flimsy and too thin to prevent cross contamination between samples on media of adjacent paper or cardboard cards, the rigidity and thickness of the present specimen collection slides 1 provide for easily and efficiently maintaining specimen and/or sample integrity on adjacent slides both during use of such slides and for extended durations. In one or more embodiments, cross contamination prevention and rigidity of the slide 1 may be further enhanced by including the third frame 30, or even four or more frames (not shown), between the two outer frames 10, 20.

The filtration media 40 implemented in the various embodiments of the invention may vary depending upon the desired or specific application or use of the resultant slide 1. In one or more embodiments, the filtration media 40 may be a flexible fibrous material, such as a flexible paper material, that is capable of absorbing a specimen deposited thereon and allowing for such specimen to dry thereon. The filtration media 40 may have a wide range of characteristics that make it suitable for its intended purpose. For instance, filtration media 40 suitable for use in the various embodiments of the invention may have differing porosities, densities, thickness, physical characteristics and physical attributes; the media may be chemically or thermally treated; the media may be untreated media; and the like. Again for purposes of illustrating the invention, in one or more embodiments the filtration media may be a flexible paper material that has a thickness of about 0.017 inches, or a thickness of about 0.033 inches, and the like.

Referring to FIGS. 1A-3C, the desired filtration media 40 is provided between two or more rigid frames 10, 20, 30, et al. In so doing, the filtration media may be cut to a size that fits within and between the first rigid frame 10 and the second rigid frame 20, whereby the media 40 preferably resides at least beyond the edges of the central opening 25 of the outer frames 10, 20 as shown by the dashed arrows extending downward from the media 40 in FIGS. 1A-B. In preferred embodiments that include the third (middle) frame 30, the filtration media 40 has dimensions smaller than the opening 25' in this third frame 30 so that the media 40 may be trapped within such opening 25'. The filtration media 40 is secured between interior surfaces of the first and second rigid frames 10, 20, and in those embodiments including the third frame 30, is preferably secured within the central opening 25' of such third frame 30.

In one or more embodiments the filtration media 40 may be provided between the rigid frames using automated equipment so as not to contact or damage the delicate composition and framework of the media 40 itself, and/or to avoid contamination of such media 40 prior to the use thereof.

At this point, the first and second rigid frames 10, 20 are securely attached to each other using a technique that does not distort or bend any portion (e.g., the outer portions) of the resultant slide 1. For instance, the frames may be attached to one another by a variety of techniques including, but not limited to, ultrasonic welding, chemical bonding (e.g., through the use of a glue, adhesive, epoxy, etc.), thermal bonding, and the like, or even any combination thereof. By attaching the first and second rigid frames 10, 20 to one another the filtration media is physically trapped between such frames.

The filtration media 40 may be fixedly attached to both the first and second frames via the foregoing attaching techniques, or it may reside securely between the frames without being fixedly attached thereto. By not fixedly attaching the filtration media 40 to the first and second frames, contamination of the filtration media by the bonding components and/or techniques may be avoided. For example, in instances where an adhesive is used to bond the rigid frames together any contamination by the adhesive onto the filtration media may detrimentally affect the usefulness of such media and the overall usefulness of the resultant slide. As such, contact between the adhesive and the filtration media is avoided.

In embodiments including one or more additional frames 30, et al. between the first and second rigid frames 10, 20, the filtration media 40 may be cut so that it fits securely inside the opening 25 within the middle frame 30. Alternatively, the filtration media 40 may be cut so that it extends just beyond the borders of the opening 25. These one or more additional rigid frames 30 between the outer first and second frames 10, 20 provide additional support, rigidity and height between adjacent filtration media 40 of adjacent slides 1. The additional frame 30 also assists in trapping or containing the filtration media in the slide without causing excessive crushing of the filtration media, and in particular, without crushing the fiber content of the media. Again, excessive damage to the filtration media may be detrimental since it would hinder the media's capabilities of absorbing any specimen deposited thereon.

In those preferred embodiments that include the third middle frame 30, the third frame 30 may be securely attached to interior surfaces of both the first and second rigid frames 10, 20 (as shown in FIG. 1B) so that the filtration media 40 is retained between these rigid frames. Again, a variety of attaching techniques may be implemented in attaching the plurality of frames 10, 20, 30 together including, for instance, ultrasonic welding, bonding, gluing, and the like. Preferably, in various embodiments the two or more frames are permanently bonded together. In one or more preferred embodiments the first 10, second 20 and third 30 rigid frames are all composed of the same homogenous material (e.g., polystyrene) such that they may be securely bonded using ultrasonic welding to form the resultant slide 1. Ultrasonic welding of these frames also prevents the need for bonding using solvent based glue and/or adhesives that may contact and detrimentally affect the properties of the filtration media, and as such, any downstream end results.

Again, in embodiments such as those shown in relation to FIGS. 1C and 1D, at least one of the outer frames (i.e., frame 20') may be provided with an opening 23 and internal ledge or lip area 24 for receiving the filtration media. This ledge or lip area 24 essentially avoids the need for middle frame 30 since the external portion of such ledge or lip area replaces the middle frame 30. The frame 20' has a thickness at its outer edges that provides the frame 20' with sufficient rigidity to avoid bending and/or damage to the resultant slide upon assembling and attaching the outer frame 20' to another outer frame 10.

FIGS. 2A-3C show alternate views of different embodiments of the present specimen collection slides 1. Referring to the perspective views of FIGS. 2A-B and 3A-B different embodiments are shown whereby each slide 1 of the invention has two or more rigid frames 10, 20, 30 securely holding and retaining a filtration media 40 there between. The filtration media 40 is exposed at this first surface (e.g. a top surface) of the collection slide 1 and is recessed within the slide 1 from a top plane surface of the outer frame 10 into the slide 1 to a depth substantially equal to the thickness 15 of such outer frame 10.

Figure 2A:
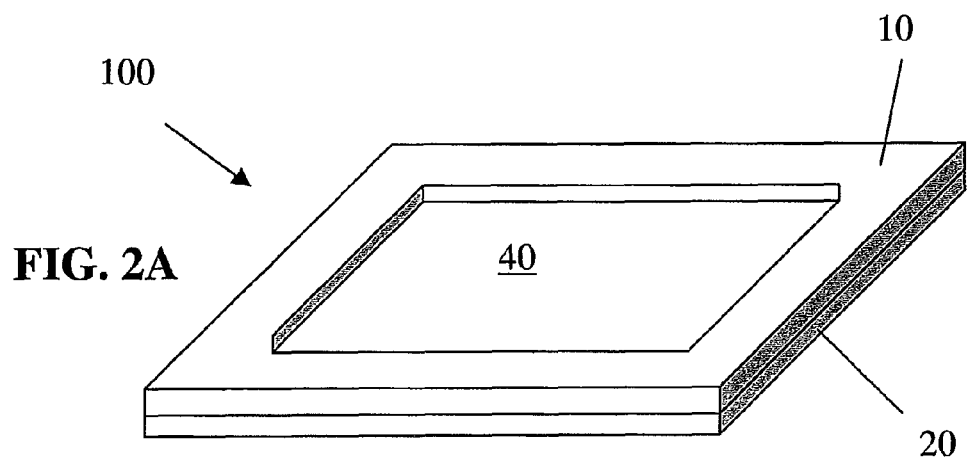
FIGS. 2A-C show perspective top and bottom views of the resultant specimen collection slide of FIG. 1A.
Figure 2B:
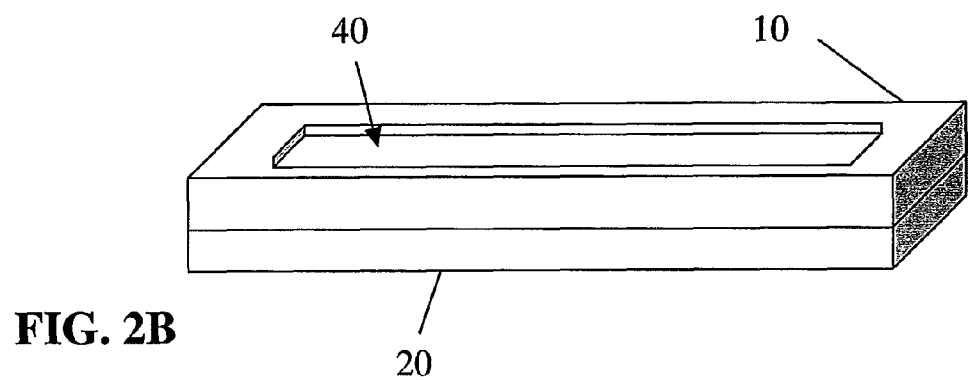
Figure 2C:
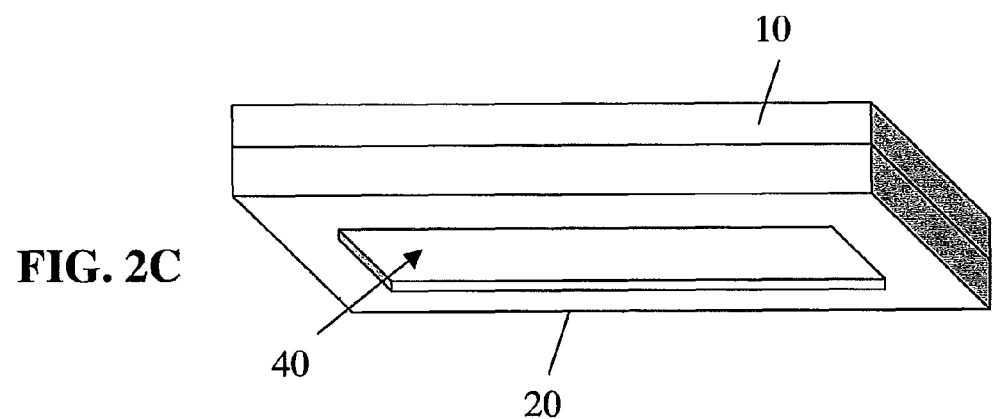
Figure 3A:
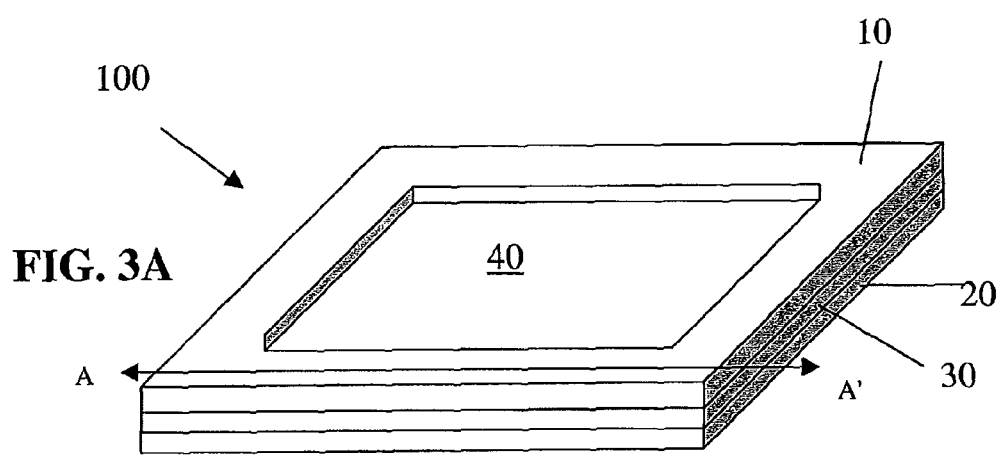
FIGS. 3A-C show perspective top and bottom views of the resultant specimen collection slide of FIG. 1B
Figure 3B:
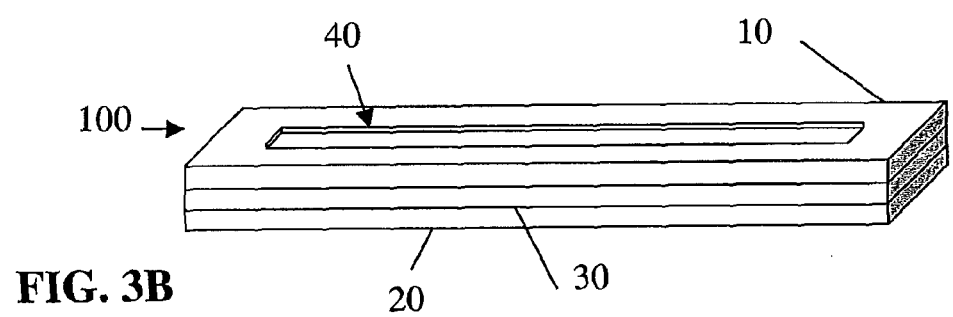
Figure 3C:
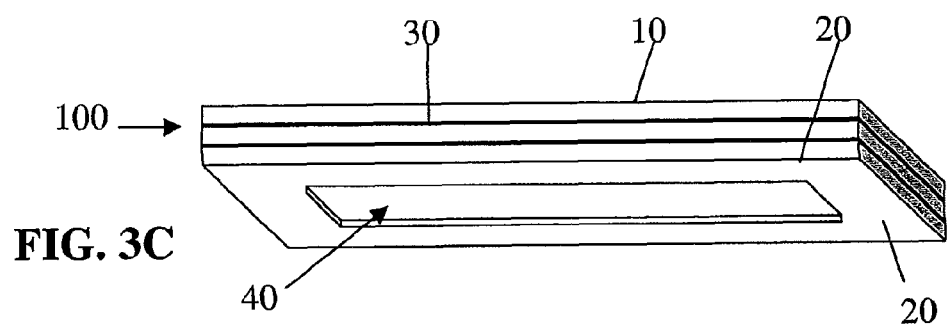

FIGS. 2C and 3C show perspective views of different slides 1 of the invention from a second surface (e.g. a bottom surface) of the collection slide 1. The filtration media 40 is also exposed at this second surface, and is recessed within the slide 1 from an outer plane surface of the outer frame 20 into the slide 1 to a depth substantially equal to the thickness 15 of such outer frame 20. Again, in this manner when the various collection cards 1 of the invention are stacked, or contact one another (as shown in FIG. 4B along line B-B'), an empty cavity 38 is formed between exposed adjacent sheets of media that has a thickness 35 approximately equal to the combined thicknesses 15 of the adjacent frames on different slides 1 (minus any thickness of filtration media extending into the empty cavity 38).

Figure 5A:
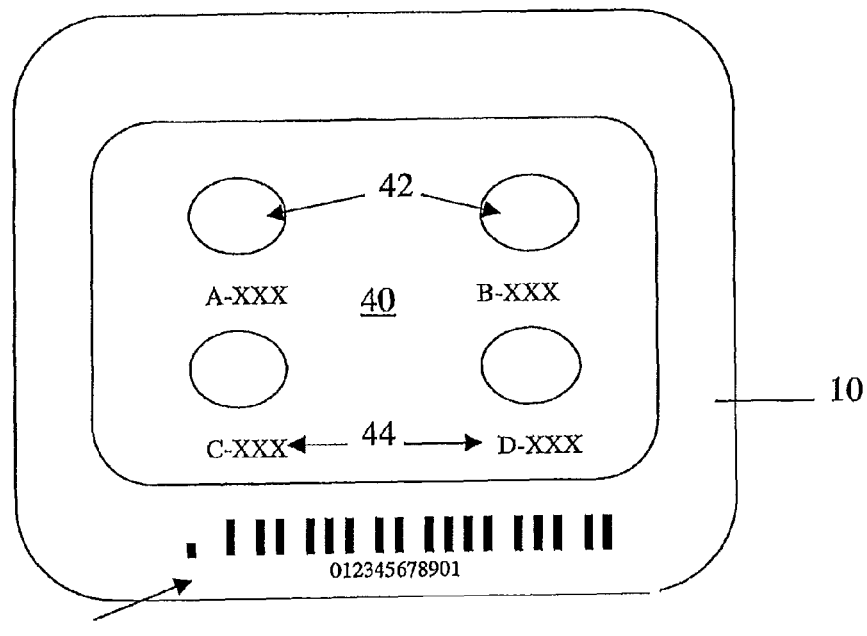
FIGS. 5A-5B show top plan views of a specimen collection slide in accordance with one or more embodiments of the invention.
Figure 5B:
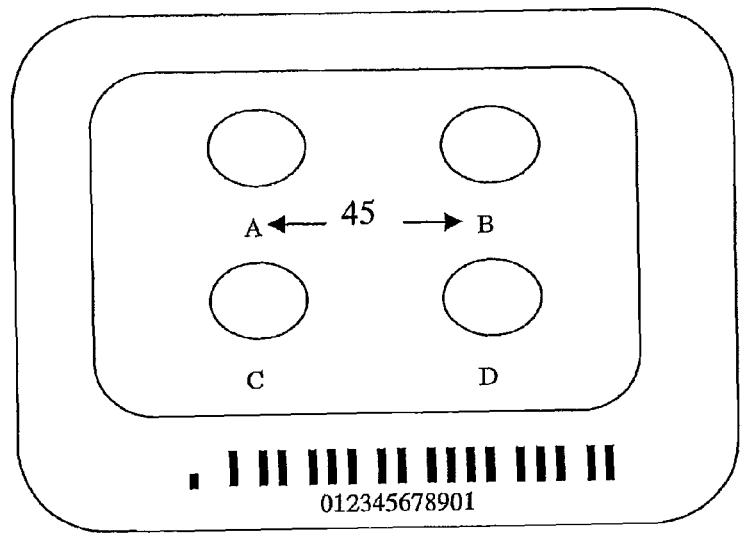

FIGS. 5A and 5B show top plan views of one or more embodiments of specimen collection slides 1 in accordance with the invention. The slide 1 is shown having filtration media 40 exposed within a recessed cavity of the rigid frame 10. It should be appreciated that due to the thickness of the outer frames 10, 20 both sides of the slide 1 (i.e., top/bottom, upper/lower, etc.) have filtration media 40 within recessed cavities of such slides 1 at the position where the central opening 25 resides.

A portion of the specimen collection slide 1 is provided with a first unique identifier 12 that identifies and distinguishes each slide 1 from other slides 1 having their own respective unique identifiers. In one or more embodiments, the first unique identifier 12 may reside on an exterior surface of at least one of the outer rigid frames 10, 20. The unique identifier 12 may be provided on the slide 1 soon after such slide has been manufactured, and is preferably not repeated for any subsequently made slides. In various embodiments the unique identifier 12 may be a 12 digit Code 128 barcode, which is an alpha-numeric code capable of providing numerous unique identifications. Each unique identifier 12 may be permanently affixed to its respective slide 1 by methods including, but not limited to, printing, embossing, embedding, engraving, staining, burning (e.g., via laser), and the like, or even combinations thereof. The unique identifier 12 preferably remains with the slide 1 from manufacture, to point of specimen source, to discard of the slide.

The unique identifier 12 on each slide 1 is different and distinct from all other identifiers 12 on any other slide, such that, each unique identifier 12 (i.e., barcode number) will only be designated once (i.e., the same unique identifier 12 (i.e., barcode number) will never be printed twice or assigned to another slide). In this manner, each unique identifier is universally distinct from other unique identifiers, making the collection of data nationwide, or even worldwide, much easier, efficient, cost effective and reliable.

Currently in the dried blood spots industry manufacturers of cards each provide their own identifier on their respective cards, whereby once a testing lab (e.g., the CDC) receives the various manufacture cards the lab often needs to include a further identifier on the card to provide a universal code across all cards received for the study. In accordance with the present invention such tedious and time-consuming tasks are avoided since each slide 1 of the various embodiments of the invention is provided with a universally distinct unique identifier at the point of manufacture. These universally distinct unique identifiers 12 also help in maintaining privacy of any supplier(s) of samples (e.g., patients) on the slides since each unique identifier is assigned to a specific supplier (patients). This makes it much easier, as compared to current practices, to completely divorce privacy data from generic database information.

The filtration media 40, which again may be pretreated with an internal standard, is provided with a plurality of predefined delineated locations 42 for receiving the specimen of choice. These delineated locations 42 may be any means that indicates where a specimen should be deposited onto the filtration media, or where a specimen has already been deposited onto the media by an automated handling system. For instance, while not meant to limit the invention, FIG. 5A shows the predefined locations 42 as four delineated circles permanently printed on at least one surface of the media, or optionally both surfaces of the media. Referring to FIG. 5A each predefined location 42 on the filtration media

40 may also be given its own unique identification 44 that distinguishes each delineated location 42 on the slide 1 from the other delineated location(s) 42 on the same slide 1, or even from one or more delineated locations 42 on different slides 1. This unique identification 44 may also be a plurality of digits using an alpha numeric 128 barcode. As such, each individual specimen collection slide 1 is provided with a primary unique identification (i.e., first unique identifier 12) and any number of sub- or secondary unique identifiers (i.e., unique identifications 44).

By providing each predefined location 42 on a single on filtration media 40 with its own unique identification 44, the present slides 1 are able to receive and retain a number of different specimen sources on a single slide 1. For instance, an entire family may be able to store dried blood spots on a single slide 1, which may be useful in genetic testing and screening, disease detection and screening, paternity testing, and the like. As an example, dried blood spots from each of a mother, father and new born may be deposited and retained on a single slide 1 for later use to test for and/or verify paternity. As another example, a drug and its various analogs may be deposited and stored on a single slide 1, which may be important for research and development of new drug discoveries. While the foregoing examples are described to help understand the novel concepts of the invention, it should be appreciated and understood that a number of possibilities exist for storing different specimens on a single slide 1.

In one or more embodiments, each unique identification 44 may be linked to the first unique identifier 12 that distinguishes each slide from other slides. An end-user of the slides 1 may further cross link the first unique identifier 12, alone or together with the unique identifications 44, to other processing identifiers that may be attached to the slide. For instance, specific sample processing identifiers may be attached to the slide at the point of sample source (e.g., a sticky back label that may include any one or more of the following: a person's name, date, time of sample acquisition, alpha characters and numeric values, etc.) in combination with the unique identifier 12 and/or unique identifications 44. In this manner, all of these identifiers help to distinguish a given slide 1 from other slides, and identify the specimens stored on such given slide from the point of obtaining the specimen sample to discard of the slide. A data log may be generated that cross links the unique identifier 12, unique identifications 44, and specific sample processing identifiers, alone or in any combination thereof, to a given slide and stored at a facility with such slide to ensure proper identification of the slide and the dried samples stored thereon.

Alternatively, referring to FIG. 5B, rather than providing a number of different specimen sources on a single slide 1 numerous samples of a single specimen may be provided onto the filtration media 40 of the present slides 1. This is often essential for recalling and retesting any given specimen. For instance, referring to FIG. 5B the four different predefined locations 42 may be provided with a single dried specimen whereby these numerous spots allow for one spot to be initially used, one to loose and two to be recalled for further testing (e.g., for result confirmation testing). This allows for the easy and accurate retesting of a previously tested specimen.

As discussed above, once the specimen collection slide 1 is fabricated it is provided with a specimen in or on its predefined delineated locations 42. The specimens collected and dried onto the slide may vary depending upon the specific end use of such specimen collection slide. These specimens may be one or more purely biological samples, one or more purely chemical samples, or the specimens may be a combination of one or more biological and chemical samples. The dried specimens may be stored on the present collection slides for 2-5 years, or even more if a stabilizer or enhancer is added either to the sample itself or the filtration media.

Figures 6A, 6B:
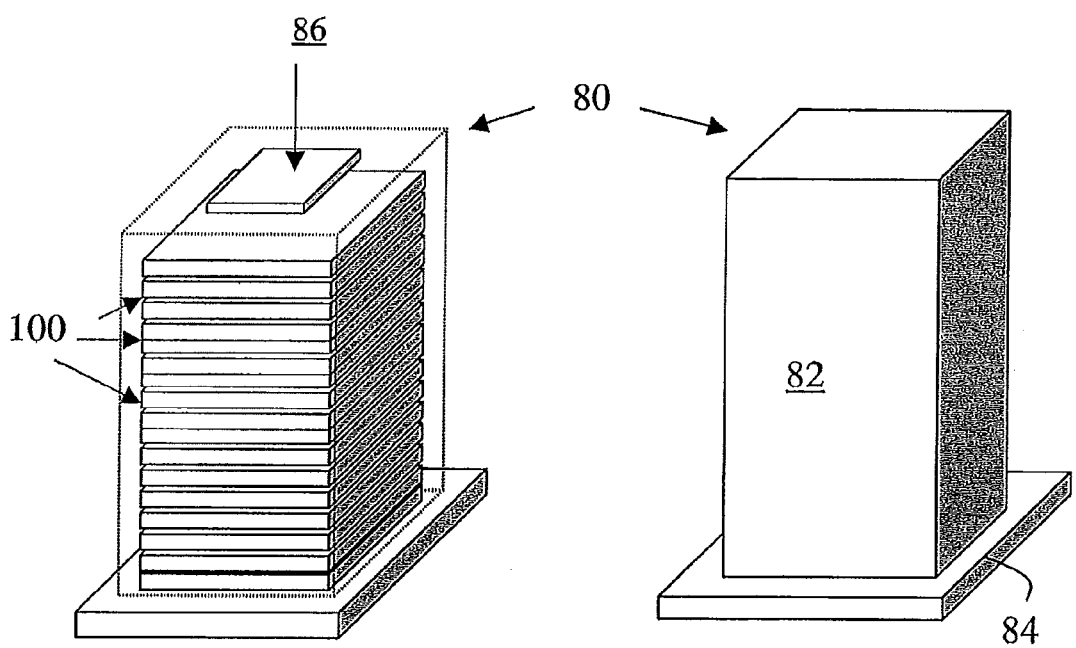
FIGS. 6A-B show perspective views of a cassette holder of the invention for retaining one or more specimen collection slides in accordance with the various aspects of the invention.

Once the specimen collection slide 1 has one or more dried specimens on the filtration media 40, these slides with their respective dried specimens must be stored in a dry environment to maintain and preserve specimen viability. Referring to FIGS. 6A-B a cassette holder 80 is fabricated that is capable of holding and storing a number of such slides 1. Each cassette holder 80 is fabricated using known techniques, such as injection molding, and is provided with dimensions sufficient for either manually or mechanically loading and unloading of a number of slides 1 therein.

The cassette holder 80 at least includes a bottom portion 84, a removable lid 82 and a desiccant 86 to maintain a dry environment for the slides 1 within the cassette holder 80. Each cassette holder 80 may also be provided with its own unique identifier (e.g., a barcode) that is linked to the slides 1 residing therein for easy, quick and efficient recall of any slide 1. When in ambient conditions for use, the removable lid 82 may cover the slides 1 residing within the cassette holder 80, but remains unsealed, to maintain a dry environment for the slides 1 within the cassette holder 80. The desiccant 86 is in an air permeable package and is equilibrated to maintain the contents within the cassette holder 80 in a dry condition when the cassette holder is in ambient room conditions for short periods of time (e.g., more or less than about 12 hours). When the cassette is returned to dry room storage conditions, for extended periods, the cassettes internal desiccant package 86 will re-equilibrate to the dry room conditions. Thus, it performs its requirement of maintaining a dry environment in the event the cassette is again moved to ambient conditions for short term processing of the cassette's slide contents.

The dessicant within the cassette holder 80 is chosen such that it preferably re-equilibrates to its surrounding conditions by itself (i.e., without any external means). That is, when in a humid environment, such as when the cassette is in ambient conditions, it will attract and absorb water vapor to keep the contents of the cassette dry. This will occur until the desiccant has reached equilibrium with the surrounding water vapor. When returned to dry room storage conditions, the desiccant will give up the contained water vapor until it is equilibrated with the dry room conditions. Thus, in essence, it is recharged to a dry condition, prior to its next move to ambient conditions.

During use the specimen collection slides 1 of the various embodiments of the invention may be automatically handled whereby a dried specimen spot is punched from the filtration media and eluted for analysis, preferably the whole sample is removed as discussed further below. The rigidity of the present slides 1 allows for the easy, fast and efficient automated handling thereof, and aids in the prevention of damage to the remaining filtration media and specimens residing thereon, as well as prevents damage to the overall slide itself. Since a variety of different filtration medias may be provided within the present slides, as well as a variety of different specimens dried on such differing media, the punched specimens may be subjected to various analytical procedures. As such, the slides 1 of the invention are suitable for use with a variety of currently available and future developed automated clinical and preclinical applications.

For instance, the various specimen collection slides 1 of the invention may be implemented in the research and development of new drug discoveries or new disease testing procedures, screening tests (e.g., neo-natal screening for congenital and inherited metabolic disorders), DNA (genetic) analyses, forensic studies (e.g., crime scene investigations, deceased identification or cause of death, etc.), immunologic studies, nutritional evaluations (e.g., in adults, children, newborns, non-humans, etc.), disease/disorder detection or diagnosis, quality assurance and quality control procedures, drug detection, and the like.

A process flow of fabricating specimen collection slides 1 in accordance with one or more preferred embodiments of the invention follows. A fully automated instrument is provided to fabricate the present slides 1 in a fully automated production line.

The automated instrument may be a walking beam system that includes an AC gearmotor with a variable frequency drive that drives the walking beam through a heavy-duty cam. As the cam drive rotates, the walking beam moves up, lifting the slide 1 components at a number of different processing stations simultaneously, and transferring them forward to the next station. The beam then drops down depositing the components on the next station to complete the next sequence of the assembly. As the beam drops down, a signal is generated that starts the action on each station. Each of the different stations runs independently. When each has completed its task, it provides a completion signal. When all of the stations report completions, the walking beam restarts with another cycle. Operating logic exists at each station for performing and completing its respective tasks, whereby the entire processing line runs automatically with minimal operator intervention.

Each of the automated instrument's different stations has independent control sequences that will be started by energizing a control relay. When the station sequence is complete, the control relay will drop out providing a normally closed contract. In one or more embodiments the process starts by energizing the drive system to apply power to the main drive motor, which moves the cam to put the walking beam to its start position to activate each station.

The first station preferably admits air to push the slide front layer (e.g., layer 10) from an incoming stacker into a first position ("position A") of the walking beam. Actuation of an optical sensor indicates that the front layer is in position A of the walking beam. If this front layer is not detected, a failure light is illuminated and the process repeated, whereby if the front layer continues to not be detected then further action on the instrument is prohibited.

The process flow continues by moving the slide middle layer (e.g., layer 30) into a second position ("position B") of the walking beam. Again, illumination of an optical sensor indicates whether or not the middle layer is at position B. The automated instrument is then provided with the filtration media.

The filtration media roll is received and threaded on a core through the instrument to its initial starting position without damaging (e.g., compressing, tearing, distorting, etc.) any portion of the filtration media. The filtration media roll may be manually threaded through to the knife. Motion and unwinding of the filtration media roll into the instrument is automatically controlled to enable precise cutting of the media into filtration media layers 40 of the slides 1. Preferably, free hanging loops control the infeed of the media into the instrument so as to eliminate tension in the roll of filtration media, whereby an electronic beam type sensor monitors the bottom of the loop such that when the beam is broke infeed of the media is stopped. The cut piece of filter media 40 is moved forward to the walking beam third position ("position C").

The slide bottom layer (e.g., layer 20) is input from an incoming stacker into a fourth position ("position D") of the walking beam. As discussed above, illumination of an optical sensor indicates whether or not the bottom layer is at position D.

After completing the above sequence, it is verified that the various layers to be provided within the assembly are present prior to welding the slide together. These layers are preferably in alignment with one another prior to welding. The presence (or absence) of each layer may be detected using an electrical solenoid that drops a measuring pin down on the finished surface to detect the presence or absence of each of the specific layers. Once it is determined that all parts are present, the assembly is moved to another station where the slide front, middle and bottom layers are ultrasonically welded together. A control relay starts an internal control sequence for welding the frames together. Preferably the welding is performed from the bottom side to prevent marking the barcode area on the front face.

At the next couple of stations a control relay actuates the barcode printing sequence controller, and then another control relay turns on the pad printer operating sequence. The completed slide is then inspected at another station, and if it is found to be defective, the defective slide is rejected. The slides are offloaded at another station from the automatic instrument into a cassette holder 80 of the invention. Once a predetermined number (e.g., 1) of slides have been loaded into the cassette holder 80, the cassette holder 80 is removed from the instrument (i.e., either manually or automatically). The instrument may be equipped to hold a number of cassette holders for the simultaneous or concurrent placement of slides therein.

Referring to FIGS. 7A-22, other embodiment of the invention are directed to uses of the various specimen collection slides 1 described above, as well as systems and methods for storing, retrieving and using dried blood spots (DBS) on the specimen collection slides 1 of the invention.

The desire and need to use DBS has been steadily rising in both preclinical and clinical applications in lieu of plasma. DBS is a dried sample of blood, typically small in size and often containing one or more analyte(s) that is stored on a slide. In typical sample analysis methods, a small portion of the DBS sample is punched from the slide. However, questions have been raised as to how the obtained sample portion relates to the total DBS portion, and if a variety of DBS locations may be selected from on a DBS slide, how to determine which DBS sample to choose and/or which portion of such a chosen DBS to punch.

In clinical trials of a new drug analyte, various patients are enrolled to test the effects of the analyte. The physical effects are monitored, but to have meaning, they must be related to the amount of analyte in the patient's bloodstream. The analyte is typically carried by red blood cells, which is measured by the patient's hematocrit. This is a measure of the percentage of the red blood cells in the bloodstream.

Currently, primarily LC-MS/MS, the analyte in dried blood spot (DBS) can be quantitated. However, when comparing the effects of the analyte on two different patients, an estimate of hematocrit is required. Patient A having a high hematocrit will show more analyte than Patient B having a low hematocrit. Thus, to compare results an estimate of the sample hematocrit is required to correctly determine the effect of the measured drug on each patient.

With dried blood spots the only resource available is the image of the blood spot, plus the available physical data including, but not limited to, volume applied, filtration media, etc. The present invention provides access to this resource(s) via independent camera systems that analyze the image from the front side where the sample was applied, and from the backside where the applied sample soaked through the filtration media.

Hematocrit levels have two defining physical characteristics, namely, color and viscosity. Fewer red cells and a lower hematocrit provide a brighter red image. It also has less viscosity. Conversely, a higher number of red cells has a higher viscosity and is noticeably a darker red. This difference in color, which is controlled through lighting in accordance with the invention, allows one to define and measure variations in color.

The other hematocrit variable is viscosity. This can be measured with various filtration media through fluid mechanics. The less viscous liquid will flow differently within the confines of filtration media. The high hematocrit, more viscous liquid, will flow in a different manner in the same media.

The problem with using color to measure hematocrit is that other factors can alter the color in a specific sample. For example, the amount of oxygen in the bloodstream. Thus, while color relates directly to hematocrit, there is not a common color scale from one patient to the next. Viscosity, however, is more directly related to the percentage of red cells, which is measured by hematocrit. By utilizing different grades of filtration media, the gathered and recorded data establishes a more defined and reliable marker for hematocrit. With sufficient data over many samples, viscosity data may be used to relate to a common color scale for various patient hematocrits. The combined data from the color results and the viscosity results provides a higher level of confidence in the ultimate end results.

In one or more embodiments of the invention, each DBS is analyzed to determine the hematocrit levels for each DBS or the hematocrit levels residing across and within a single DBS. A high hematocrit in the DBS sample corresponds to such DBS sample having a large amount of red blood cells, as compared to a DBS sample having a low hematocrit. Red blood cells absorb more analyte as compared to white blood cells. As such, a DBS sample or portion thereof having a high hematocrit will have more red blood cells, and in turn, more analyte.

In accordance with other embodiments of the invention a DBS retrieving and sampling system is provided having dual camera systems for imaging and analyzing a DBS prior to taking a sample there-from. In one or more embodiments, a first camera system of the present systems is positioned over a first side of a DBS slide (i.e., a front side of the slide) while the second camera system is positioned over an opposite, second side of the DBS slide (i.e., a backside of the slide). As discussed in more detail below, each separate camera system at the front and back of the slide has at least its own independent lighting control.

For bioanalytical evaluation of dried blood spots, embodiments of the invention capture one or more images of a DBS on a slide, both at the front side and backside of the slide. That is, a number of different images of each DBS may be taken at the front and back of the slide. For each of these images, processing parameters of each respective camera may be adjusted to capture images using a variety of imaging effects to obtain additional data of the DBS. These imaging effects may include taking images at various adjusted camera controls including, for example, gain, color, hue, brilliance, and the like. In doing so, both cameras will detect and capture additional imaging data detail (e.g., color/hue differentials within the sample) that otherwise would not be available to the naked eye. Camera controls may also be adjusted by changing imaging pixilation to capture various images at different pixels. This captured DBS image data may be used to calculate the area of the actual DBS deposited onto the slide.

The captured image(s), along with various image data, are stored in a database of the present DBS sampling systems for analysis thereof. This dual-captured DBS imaging data is evaluated to determine a number of parameters including, but not limited to, whether the sample soak into the slide, whether the sample spread-out on the slide, color/hue differentials within the sample, and the like. It should be appreciated and understood that various other parameters of the captured DBS images may be analyzed in accordance with the invention depending upon the desired end result.

The captured image(s) and the analyzed parameters of such captured images are used to select the specific area of the DBS on the slide to be sampled prior to the analysis thereof. Depending upon the end-analysis that is to be performed on the DBS, one, more and/or various combinations of the analyzed DBS imaging parameter data may be used to determine the exact DBS location on the slide to punch for analysis.

For instance, red cell levels of the blood sample are often crucial since high red cell levels reflect high levels of analyte absorbing red blood cells. In instances when it is desired to test a blood sample for an analyte of interest, a DBS sample location having high red cell levels may be desired as such a punched location will provide easier analyte testing and more reliable test results thereof. The present invention analyzes the captured images, from both the front and back of the slide, by analyzing detected image parameters thereof. In doing so, the invention determines those locations of the DBS sample that are darker in hue (color) and less brilliant, both of which reflect regions of the DBS sample having high red cell levels. These regions of the DBS sample having high red cell levels may be selected and punched for analyte analysis.

The invention also utilizes other DBS parameters for determining where to punch the DBS slide. In addition to determining those DBS regions having high red cell levels, the invention also analyzes absorption patterns of the blood sample on the slide prior to punching. Blood samples having higher red cell levels are more viscous than blood samples having low red cell levels. The dual images captured at the front and back of the slide include pixel data, which is used to determine the flow pattern of the sample through the filtration media of the slide prior to punching. For instance, the pixel data at the front and back of the slide may be used to determine whether the deposited blood sample spread out and/or soaked through the filtration media, both of which are parameters used in accordance with the invention to determine where to punch and obtain a suitable sample from the DBS for subsequent analysis thereof.

Other factors are taken into consideration in the determination of flow pattern of the sample through the slide filtration media. Predetermined or known properties and characteristics of the filtration media of the slide are input into a computing device of the invention and used in the determination of flow pattern of the sample through the media for selecting a location to punch. In one or more embodiments, the properties and characteristics of the filter media may include porosity and thickness of the filtration media, both of which affect flow characteristics of the various samples through the filtration media, particularly in view of the different viscosities of such samples.

Another factor implemented in determining a location to punch is the total of volume of sample deposited onto the filtration media. With the volume of deposited sample being a known variable prior to depositing, the present system may calculate the percentage of the total sample that was actually analyzed. Again, the dual camera systems of the invention capture and measure the entire sample area at both of the front and back of the filtration media. Often, the front and back pixel areas of the samples are different with the front (or deposition side) of the media having the sample dispersed over a larger surface area as compared to the back of the media. Once deposited, the sample may tend to flow through the media in a conical shape. Knowing the thickness of the filtration media and the sizes of the surface areas of sample at the front and back of the media, the invention calculates an approximate saturation volume area of filtration media saturated with sample. In doing so, a frustum of a cone volume area is estimated within the filtration media, which may also be used in determining the exact location to be punched for sample removal.

It should be appreciated and understood that a number of other parameters and variables may be used to determine the exact location on a filtration media where a sample is to be removed (e.g., punched). It should also be appreciated and understood that the invention may further include a calibration period during which a closed control logic feedback loop determines a best location for removing samples for a batch of filtration media slides to achieve a desired end result test analysis (e.g., a desired output analyte recovery). This closed control logic feedback loop may use input parameters that will provide optimal output results (e.g., optimal recovery of an analyte).

This calibration period may be achieved through end-user (i.e., operator) input in combination with system logic. For instance, the dual cameras may display to the end-user images of one or more deposited samples at both a front side and backside of the slides. The end-user may select a desired area for spot selection. The camera software defines and records the image details of the selected spot, and then such selected spot is punched and analyzed. The end results are rated by the operator and recorded within software of the invention. Over a period of time involving the processing of a number of samples, a correlation between input parameters and output results is obtained for determining best locations to punch samples. Once it has been determined that optimal end results have been achieved, correlation between such optimized results and the locations on the slide at which the samples for such optimized results were taken from the slide are identified and stored for subsequent sample analyses.

Without departing from the novel concepts of the invention, while the invention is described herein with respect to blood samples (i.e., dried blood spots (DBS)), the invention may be implemented with any type of sample suitable for use with filtration media slides. A variety of dried matrix spots (DMS) may reside on a filtration media slide, and may be used in the present invention. These DMS may include one or more purely biological samples, one or more purely chemical samples, or the specimens may be a combination of one or more biological and chemical samples. For instance, a purely biological sample may include, but is not limited to, blood, saliva, bodily secretions (e.g., tears, synovial fluid, urine, semen, etc.), organic matter, and the like. A purely chemical sample may include, but is not limited to, a drug, an analyte, an organic or inorganic chemical compound, and the like. A sample that includes both biological and chemical components, may include, but is not limited to, a blood sample being tested for presence of a drug, bodily secretions being tested for presence of an organic or inorganic chemical compound, such as, a contaminant (e.g., a poison), and the like.

Referring to the drawings, dried blood spot (DBS) samples are provided on filtration media slides. FIG. 7A shows an example of such a filtration media dried specimen storage slide described above and in U.S. patent application Ser. No. 12/868,229 (incorporated by reference herein).

The filtration media slide (1) may include outer rigid frames (10, 20, 30) that encase a sheet of filtration media (40), which is trapped within the ultrasonically welded assembly. For instance, three die cut forms (10, 20, 30) of high impact polystyrene 0.030 inch sheet material may be ultrasonically welded to form the slide (1). Since the slide may contain various filtration media for specific applications, the specific designation of the filtration media (5) may be printed on the slide.

Also the name of the slide manufacturer (4) may be printed on the slide, along with the unique identifier 12, e.g., an 12-digit 128 bar code, for sample identification. These unique identifier 12 bar codes may be both machine and human readable. The combination of manufacturer's name and the 128 bar code, combined with the manufacturer's agreement to never print the same identification number twice on this product, assures that there is one positive sample identification from source to discard. This is an essential requirement in a Good Laboratory Practice (GLP) regulated environment.

To avoid the use of soluble ink, all printing on the polystyrene surface may be accomplished with laser markings to provide permanent identification markings both on the rigid card material itself and on the filtration paper. Laser printing also avoids contact pressure, which may alter the filtration characteristics of the filtration media. A laser may be used to mark the suitable sample targets. The laser is a non-contact printing method that leaves a light scorched marking for identification on the filtration media and/or etching a permanent barcode identifier in the polystyrene frame of the slide. In addition, the laser avoids the use of soluble inks, which may dissolve, dissipate or smear upon depositing the specimen (i.e., organic and/or inorganic specimen) onto the media. By controlling the power applied with the laser, it may be used to simply mark, or it may be used to cut a pattern by burning through.

Additionally, by increasing the power to the laser, the laser may burn through the filtration media in a precisely controlled manner to provide cut out sections in the filtration media which both mark locations where sample specimens are to be deposited and provide for easier and more efficient removal of such marked locations. For instance, after the laser cuts through the media, filtration media portions may remain as holding tabs at the 12:00, 4:00, and 8:00 o'clock positions.

As shown in FIG. 7A, the filtration media (40) may be printed with a number of predefined delineated locations 42, e.g., regions A, B, C, D, that identify locations where a sample is to be deposited, or has been deposited, thereon such media. As discussed in the previous paragraph, in one or more embodiments these delineated locations 42 may be predefined by providing cut out sections of the filtration media to both mark locations where sample specimens are to be deposited and provide for easier and more efficient removal of such marked locations. As shown by the dashed lines in original FIG. 7A, a number of cut out perforations 7 may traverse through the filtration media 40 to predefine the location where samples are to be deposited onto the filtration media. These perforations may be cut into and through the thickness of the filtration media (e.g., by use of a punch, mechanical punch, cutting device, etc.), or they may be scorched (burnt) into and through the thickness of the filtration media (e.g., by use of a laser, etc.).

In one or more embodiments, two or more cuts may be made through the filtration media to provide a delineated location where sample is to be deposited onto the filtration media. Preferably, three (3) cuts are provided through the filtration media to define a delineated location 42 that has filtration media holding tabs at 12:00, 4:00, and 8:00 o'clock positions, more preferably six (6) cuts are provided through the filtration media, and most preferably nine (9) cuts are provided through the filtration media to generate each delineated location 42. For instance, in one or more embodiments each delineated location 42 may have nine (9) cuts formed in a 6 mm diameter through the filtration media (see, e.g., the perforations in FIG. 7A as delineated by the dashed lines). In accordance with the invention, these cuts out sections of the filtration media 40 of each slide 1 generate delineated perforated sample location(s) 42 for sample deposit.

A sample, e.g., a blood sample, is deposited onto each delineated perforated sample location 42 such that the sample is retained within such location 42 due to the cut out media sections forming isolated sample locations 42. That is, the perforations provide a physical barrier for fluid flow through the filtration media, whereby often the entire limiting area of each location 42 is filled with sample and such liquid sample retained within the perforated location 42. This entire sample within the perforations may then be easily removed for analysis by breaking remaining filtration media tabs.

For ease of understanding the invention, blood is used as the sample provided onto and within the perforated sample location 42 to generate a perforated dried blood spots (PDBS). Once ready for use, the entire sample spot, that is, the whole cut out delineated location(s) 42 containing sample, is removed for elution and/or recovery, rather than merely an aliquot or ⅛ inch punch portion of a sample location as is done in the prior art. By taking the whole sample, as compared to a ⅛ inch punch (which is not indicative of the whole sample), the chromatography of the analyte may be analyzed as it moves through the filtration media. In one or more embodiments, nine (9) cuts or perforations are formed in the filtration media to provide delineated perforated sample locations 42 having a 6 mm, which is 3.56 times the area of a currently used ⅛ inch punch based on $\pi r^2$, resulting in the ability to remove and analyze the whole sample location 42.

Figure 7E:
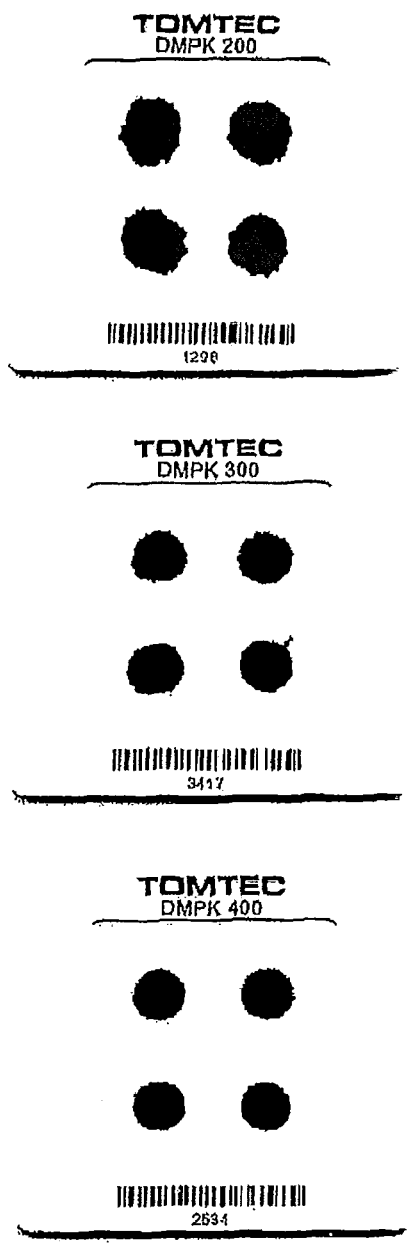
FIG. 7E shows a number of front side (top) and backside (bottom) views of sample spot images taken in accordance with one or more embodiments of the invention.
Figure 7E:
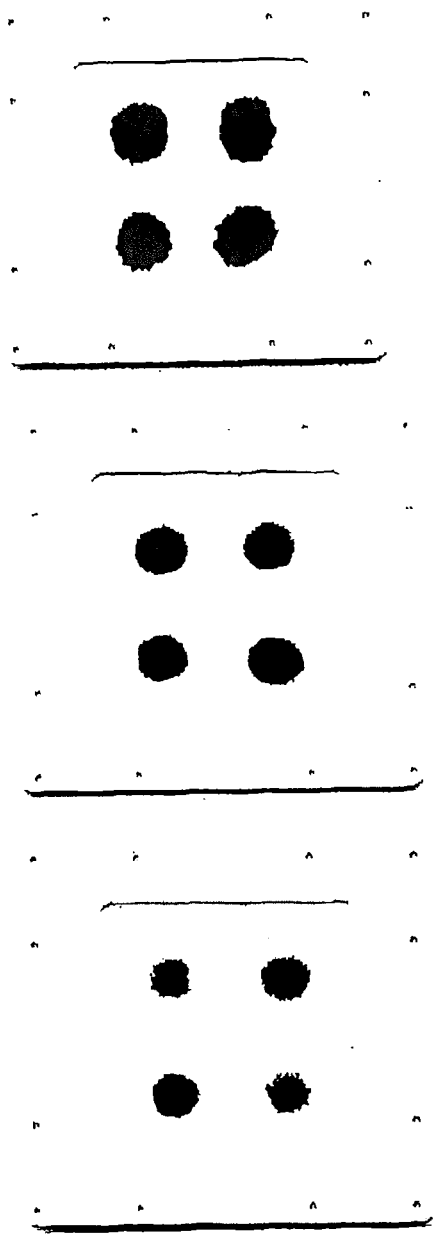

Referring to FIGS. 7B-7E, various views of a sample loaded are shown onto a filtration media slide (1) in accordance with one or more embodiments of the invention. As is shown, a front side (i.e., top) of the slide is shown in FIG. 7B, which is the side that the sample (1) is deposited onto the media (40). As the sample (1) is absorbed into the filtration media, properties of such sample may cause the sample to spread out over the surface area of the top of the media as it is absorbed therein. FIG. 7D shows the backside (i.e., bottom) of the deposited sample (1) of FIG. 7B, while FIG. 7C shows a cross sectional view of the sample (1) traversing through a thickness of the media (40). As is shown, the sample absorbs into and through the thickness of the media in a conical shaped pattern. In doing so, the absorbed sample (1) at the back of the media may have a smaller surface area as compared to the sample surface area on the front side of such media.

Again, using these front side and backside sample surface areas obtained in accordance with the invention, the invention estimates the frustum of a cone volume area within the filtration media to identify a location of the absorbed sample that will provide a sufficient sample size with the desired characteristics for the removal thereof. FIG. 7E shows front side (top) and backside (bottom) views of images taken in accordance with the dual camera system of the invention. As is shown, the sample absorbs differently into and through the filtration media depending upon the characteristics and properties of the media itself, as well as depending upon the characteristics and properties of the sample being absorbed therein filtration media.

Figure 8:
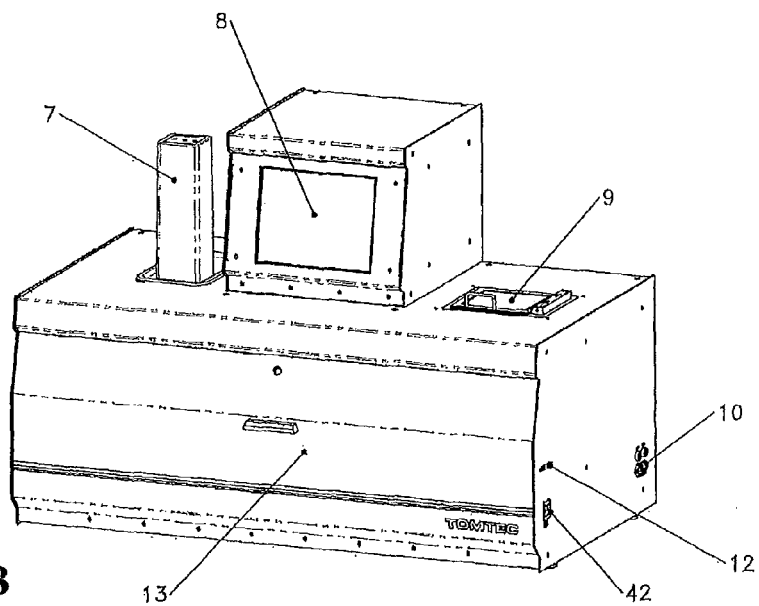
FIG. 8 is a perspective view of an automated filtration media handling system in accordance with one or more embodiments of the invention.

FIG. 8 is a perspective view of one or more automated handling processing systems in accordance with the invention. These systems include hardware, software and logic running on such systems for handling and processing filtration media slides (1) in accordance with the invention. The incoming sample slides may be contained and transported within a cassette (17) that holds numerous incoming filtration media slides (1). For instance, the cassette (17) may hold up to about 96 slides. A full color electronic display (18) may be used by the system software control to display results to the end-user/operator.

The systems also include a receiving rack of 96 pipettor tips, or a standard 96 well microplate, which may be operator loaded and retrieved through an access door (19). AC power may be provided by an external fused connection (110). A power on-off switch (142) may be provided as are multiple USB ports (112) for connection to and interface with the on board control system. A front access door panel (113) may be provided for maintenance purposes.

Figure 9:
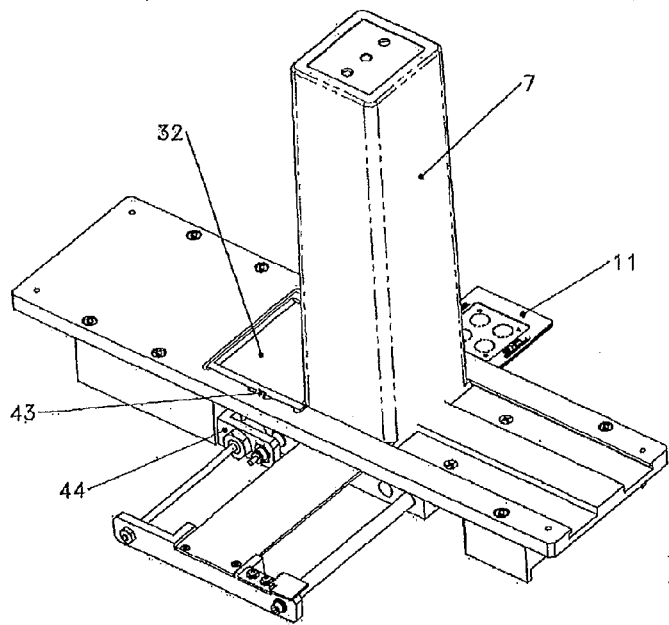
FIG. 9 is a perspective view of a cassette in feed section of one or more embodiments of the invention.

Referring to FIG. 9, a perspective view of the cassette infeed/outfeed station is shown with the cassette (17) of slides placed on the station. The cassette may be moved forward. As the cassette is moved to the infeed/outfeed positions, the cassette lid (132) is retained by mating tabs and slots (143). A controlled pneumatically driven slide component (144) moves an incoming sample slide (111) containing a sample to be processed to a first imaging position (146), as is shown in FIG. 10.

Figure 10:
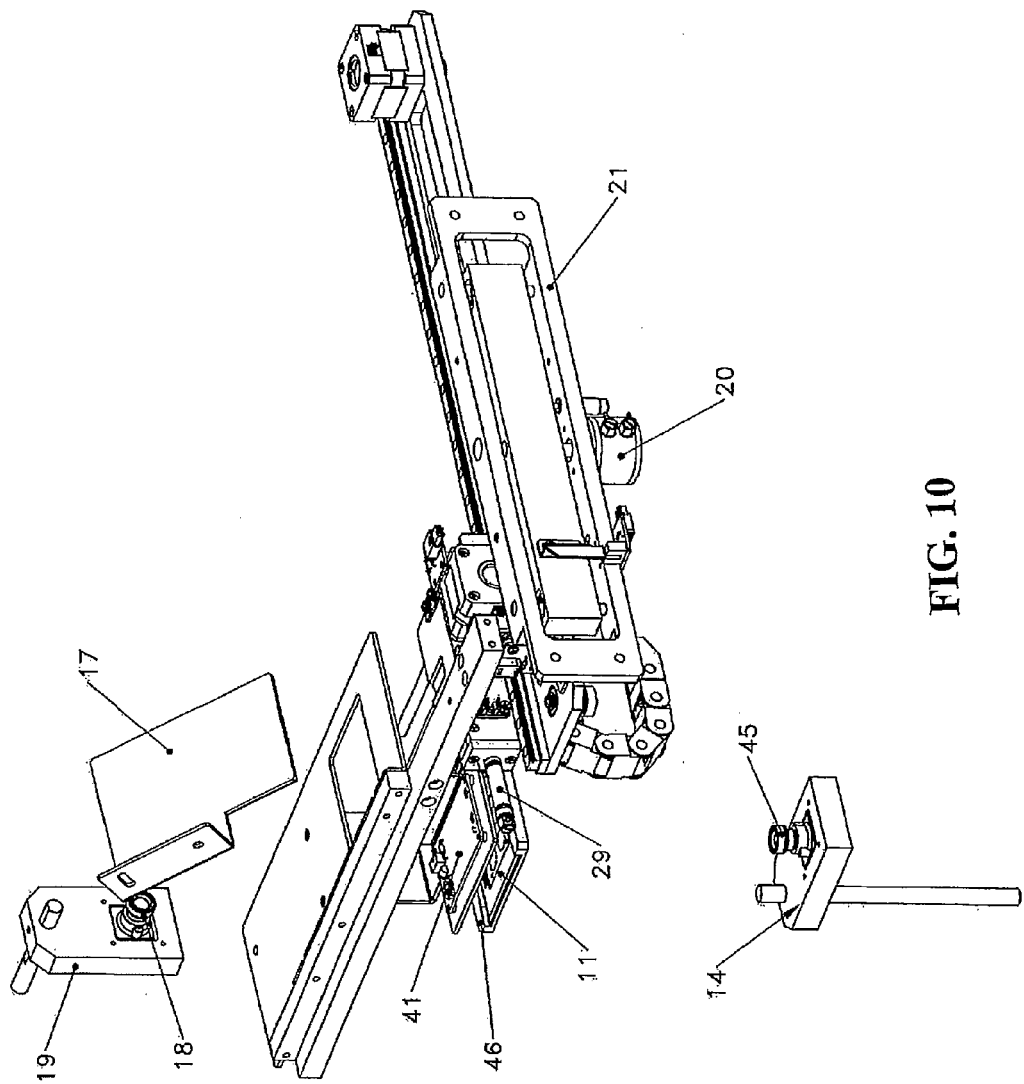
FIG. 10 is a perspective view of a lower camera (backside camera) of the dual camera system of one or more embodiments of the invention.

FIG. 10 is a perspective view of the backside (i.e., bottom side) camera station of the present systems having dual camera stations, one at the front side and the other at the backside of the slides to be processed. As is shown, a software controlled LED lighting assembly (141) provides controlled illumination to the front side of the incoming sample slide (111). At the opposite backside of the incoming sample slide (111) resides the bottom side camera (145). The bottom side camera (145) is mounted at a focal length to image the backside (i.e., bottom side) of the incoming sample slide (111). Another software controlled LED lighting assembly (114) provides controlled illumination to the backside of the incoming slide (111) for capturing such image.

Figure 11:
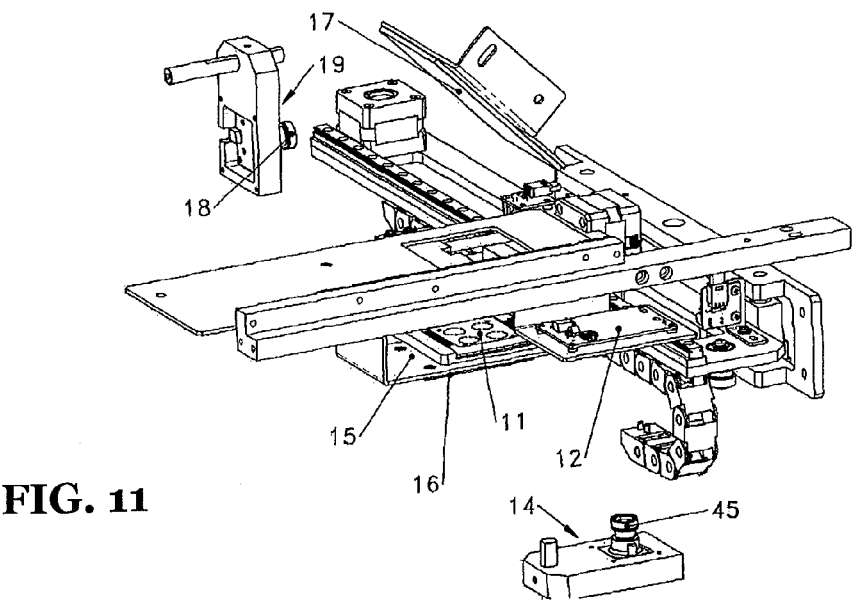
FIG. 11 is a perspective view of an upper camera (front side camera) of the dual camera system of one or more embodiments of the invention.

After the image of the backside of the sample slide (111) has been obtained, the sample slide (111) is moved to a second imaging position to image the opposite side of the slide. Referring to FIG. 11, the sample slide (111) is moved to second imaging position (115) for imaging the front side of the incoming sample slide. This second imaging position (115), or station, also includes a software controlled LED illumination system (116) to illuminate the backside of the incoming slide for capturing the slide's front side image. As shown, the slide (111) is positioned over the backside illuminator (116) for capturing the front side image.

In accordance with the invention, for both front side and backside imaging, during the process of taking such images the lighting assembly on the opposite side of the camera taking the photograph of its respective side is turned on during such imaging to capture color variations within the spots. That is, when photographing the backside of the incoming sample slide (111) only the front side lighting assembly (141) is illuminated while the backside camera captures an image of the spot on the filtration media backside. Conversely, when photographing the front side of the incoming sample slide (111) only the backside lighting assembly (116) is illuminated while the front side camera captures an image of the spot on the filtration media front side. An additional imaging process may also need to be taken of the front side of the slide using both the front side (141) and backside (116) lighting assemblies to capture any identification information residing on the slide front side (e.g., bar codes, sample identification code, etc.)

While the first and second imaging positions or stations are described as respectively obtaining backside and front side images of the slide, it should be appreciated that the first imaging position may capture the front side while the second imaging position captures the backside of the slide (111). Due to the instrument height limitations and the front camera focal length, a mirror (117) may be used to image the slide front side. As with the backside camera, a similar LED illumination system (119) may provide front side illumination for the front side camera (118).

Figure 12:
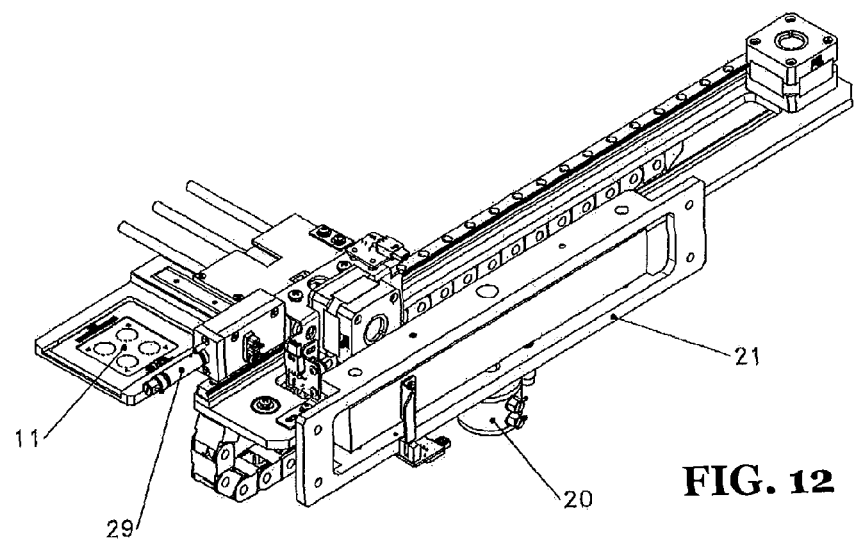
FIG. 12 is a perspective view of a transport component for transporting incoming sample slides into the present systems.

FIG. 12 shows the transport component of the present systems for transporting incoming sample slides (111) to various positions and stations in x-y-z-directions within such systems. The transport component may include two stepper motors that provide controlled positioning motion in both the x and y directions. The transport component is able to move in the z-direction via a small pneumatic cylinder (120) to allow for moving the slide (111) into a punching position.

When the slide (111) is presented to the punching station, there must be clearance to insert the slide between the punch and mating die. However, to punch the desired x-y coordinates of the filtration media, the media must be in physical contact with the surface of the die to avoid tearing the filtration media. This required z-motion is provided by the air cylinder (120). It moves the x-y bridge assembly vertically within the supporting framework (121).

Figure 13:
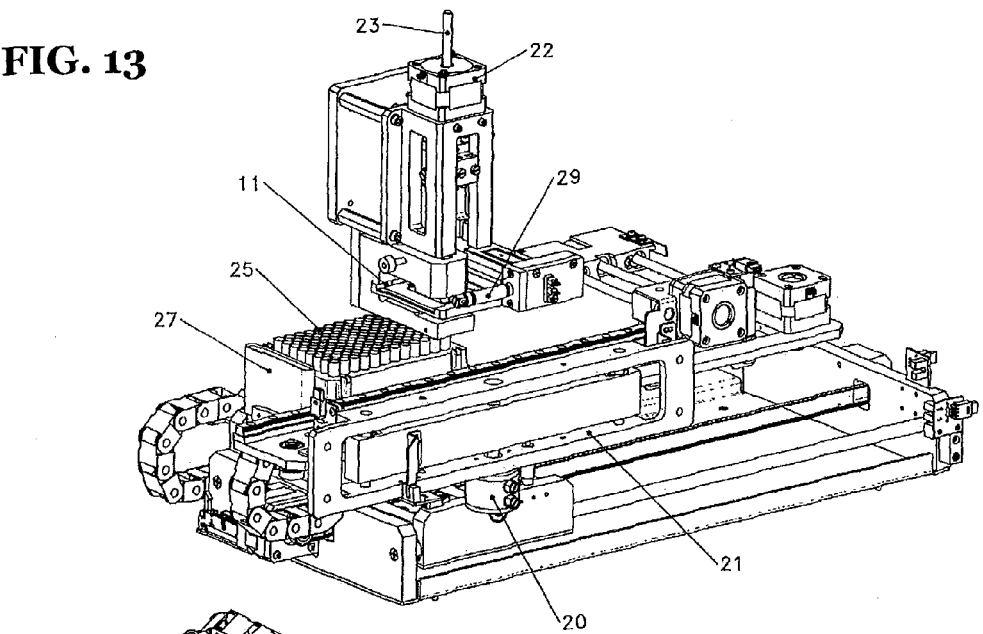
FIG. 13 is a perspective view of a punch assembly of the system of one or more embodiments of the invention.

FIG. 13 shows a perspective view of the punch assembly of the invention. The punch assembly includes an axial stepper motor drive (122) that moves the punch assembly (123) through the sample slide (111), through the mating die and into the receiving receptacle below. The punch has a central hole through which a low power laser shines.

This central hole may also be connected to a vacuum source and a source of low air pressure (not shown). The stepper motor control positions the punch, and at the point of contact between the punch face and the filtration media a solenoid valve applies vacuum to the central hole of the punch. The vacuum assists in holding the punched chad (piece) to the face of the punch for transport to the receiving location. Concurrently, the vacuum source is applied to small holes surrounding the die (not shown). The purpose is to capture any airborne particulate matter that is discharged by the punching action. This vacuum assisted airflow is discharged to the atmosphere through a HEPA type filter to capture infectious material.

At the bottom of the punch stroke the vacuum in the central hole is replaced with a puff of positive air pressure to assist in discharging the punched chad into the receiver. The punch withdraws sufficiently to allow the receiving receptacle to move clear of the punch. This allows the low power laser shining through the bore of the punch to illuminate a sensor that verifies to the system logic that the punch and sample transport and receipt have been completed.

Figure 14:
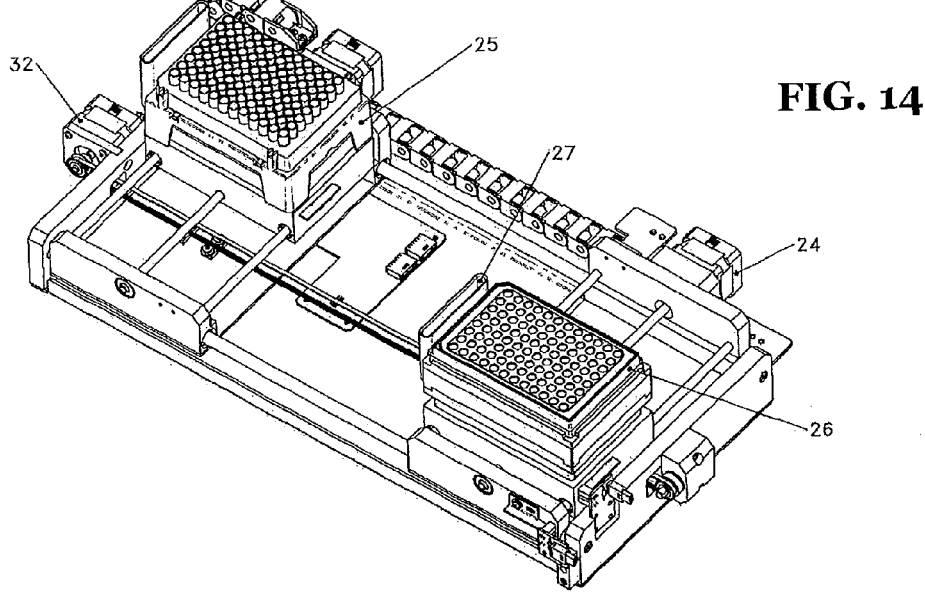
FIG. 14 is a perspective view of an x-y bridge system of one or more embodiments of the invention.

FIG. 14 shows the x-y bridge system for the receiver of the invention, which includes two stepper motor drives for positioning control. One motor (132) provides controlled motion in the x direction, while the other motor (124) provides controlled motion in the y direction. The carrier may accommodate a rack of 96 pipette tips (125), or it may accommodate a standard 96 well microplate (126). The receiving well, or tip, is properly positioned by the associated software and electronic controls of the present systems.

When punching samples from filtration media with the same punch and die systems, there is always a concern about sample carry-over between samples. To avoid these problems the present systems and methods include a step of punching a blank area of filtration media to assist in cleaning the system to minimize the possibility of sample carryover. A trash receptacle (127) of the present systems is moved into position by the receiving bridge system to capture the punched chad.

Figure 15:
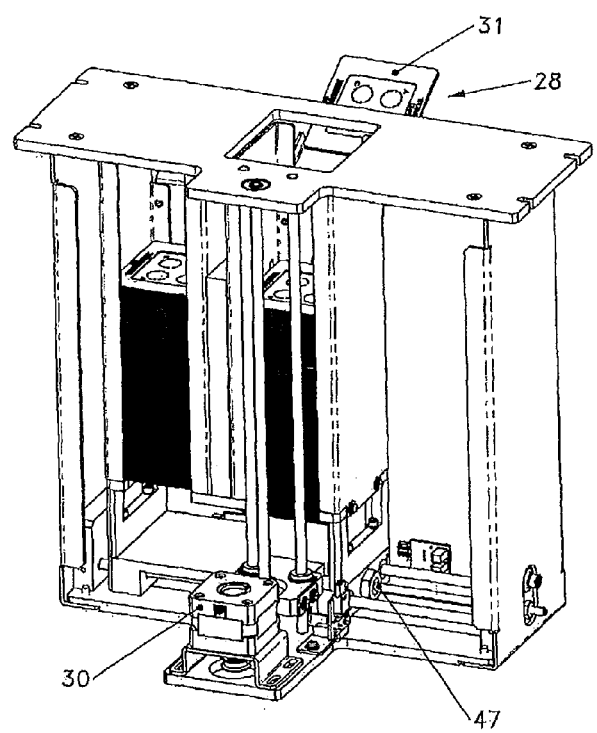
FIG. 15 is a perspective view of an output stack assembly of one or more embodiments of the invention.
Figure 16:
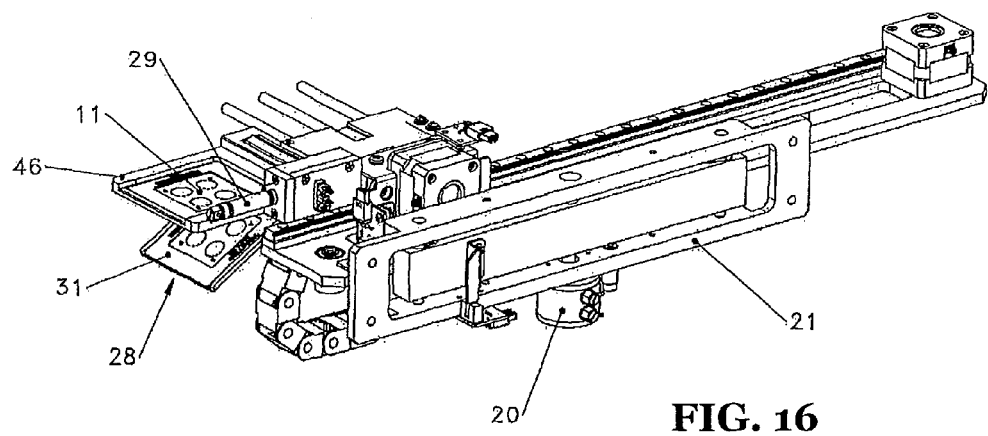
FIG. 16 is a perspective view of a slide handling x-y-z assembly of one or more embodiments of the invention.

After the punching cycle is complete, the slide is returned to the front side camera station (146). A second front side image may be captured to document the location of the sample that was punched. The slide (111) may then be moved to the offload position, as shown in FIG. 16. In offloading the processes sample (111), an air cylinder (129) rotates the slide carrier from position (146) to position (128) to allow the slide, now shown as (131), to move down into the receiving output stack. FIG. 15 shows the output stack assembly. Preferably, slides are then filed and stored within the cassette in their original filing order. The output stack assembly may include two stacks for controlling the height (i.e., amount) of slides within the present systems.

Figure 17:
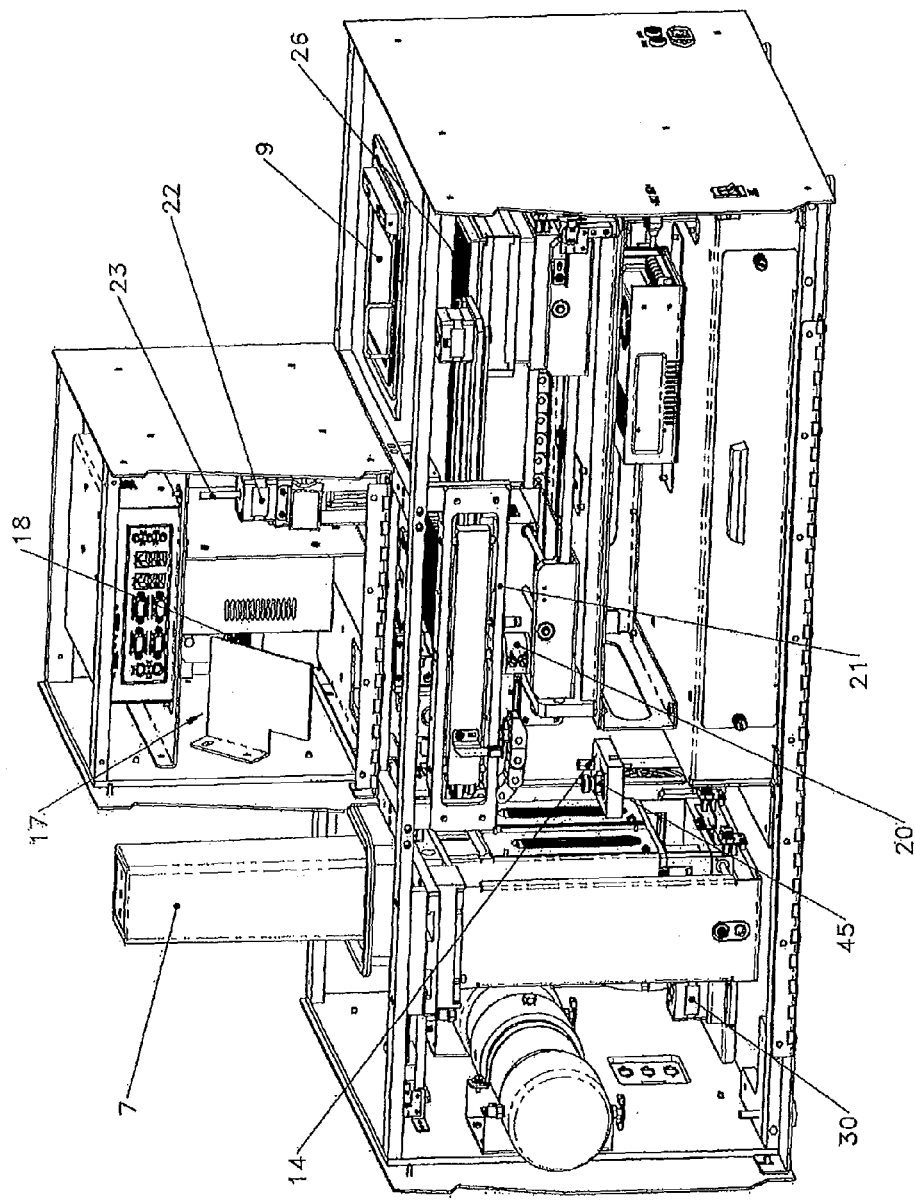
FIG. 17 is a perspective view of an assembled system of one or more embodiments of the invention having front enclosure panels removed to show the relationship of various described sub-assemblies or parts of such system.

As the slide carrier (128) drops down to its offload position, the slide (131) it contains drops into the waiting receiver stack. A software controlled stepper motor (130) keeps the receiving stack at the correct height to allow the returning slide (131) to glide in on top of the current stack. This action maintains an orderly stack of receiving slides. When one receiving stack is at its capacity, a pneumatic control system (147) shifts the other stack into position to receive slides. When both stacks are at capacity, the slides are returned to the incoming cassette, which is still in position as shown by FIG. 17.

Once the punched portions of sample slides are removed from the present systems, they may then be used for subsequent analysis such as, for example, analyte recovery. Alternatively, the systems of the invention may be combined with another analytical tool for the directed use of such punched sample. For instance, the systems of the invention may be combined with chromatography instrumentation for the direct elution of the samples immediately after being punched and removed from the slide (111).

As an example, the sample may be directly eluted into the mobile phase of a liquid chromatography (LC) instrument, which is commonly part of an LC/MS/MS analyte detection system. For such an application, the x-y recovery bridge system shown in FIG. 14 may not be utilized or installed, nor is the punch system of FIG. 13. Both are replaced by a break in the liquid connection of the mobile phase going to the LC instrument, as is shown in FIG. 16.

Figure 18:
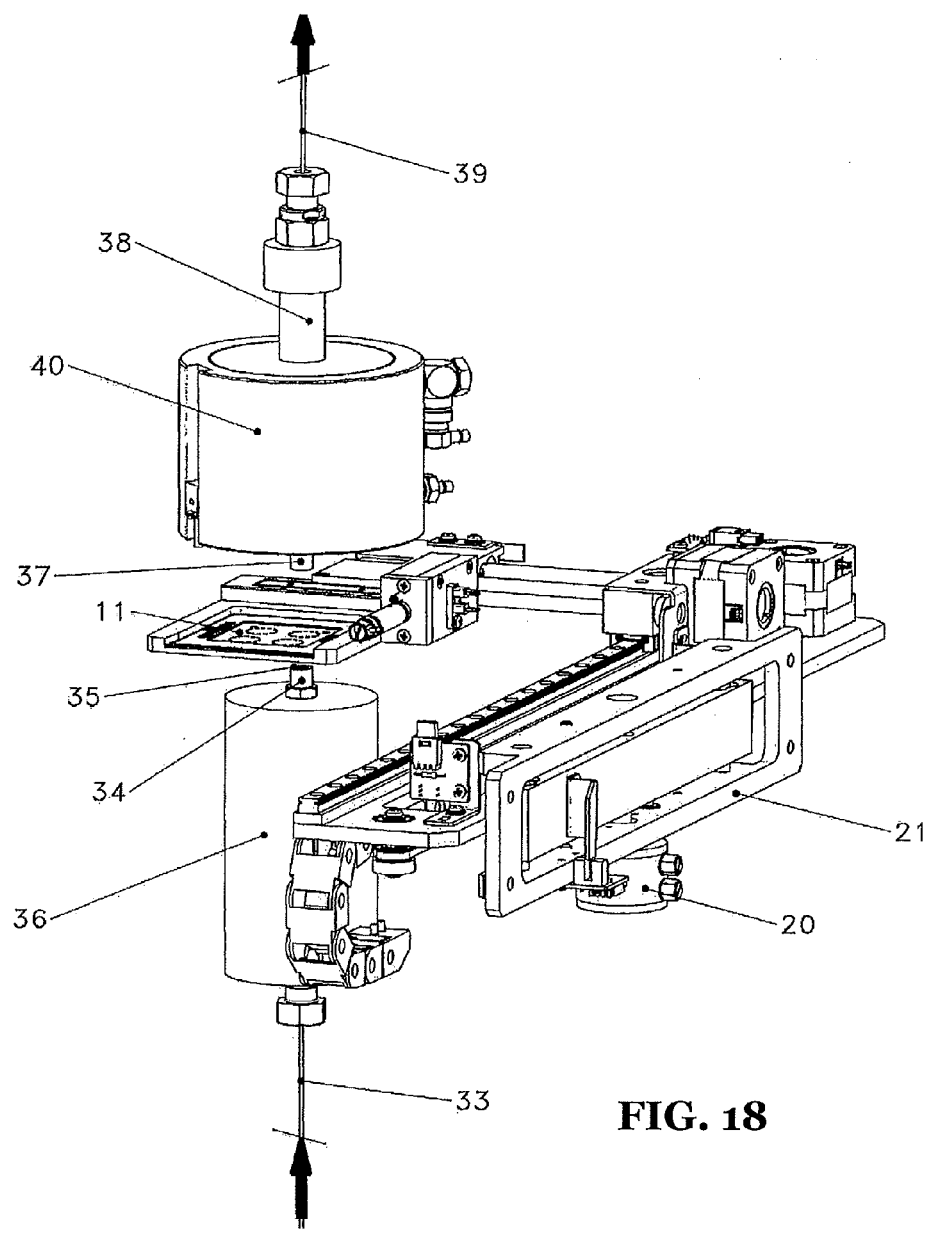
FIG. 18 is a perspective view of a liquid chromatography interface in combination with the various systems of the invention.

Referring to FIG. 18, the incoming side of the mobile phase line (133) terminates at a connection point (134) that is surrounded with an elastomeric O-ring (135). This elastomeric O-ring (135) is mounted on a rigidly mounted support column (136), which is affixed to the instrument framework. The outgoing mobile phase line (139) terminates in a mating elastomeric O-ring (137) that is positioned by the central plunger of a large bore air cylinder (140). The air cylinder may apply sufficient force to cause the mating elastomeric O-rings to create a seal that is sufficient to withstand the internal pressure of the mobile phase.

Still referring to FIG. 18, the selected spot for analysis on the incoming slide is positioned between the mating O-rings by the x-y-z, bridge system (121). When the selected spot is aligned between the O-rings, the air cylinder (120) lowers the incoming sample slide (111) so that the selected spot is in contact with the lower O-ring (135), which is rigidly supported by the column (136). At this point, the control system applies air pressure to the air cylinder (140) causing the top O-ring (137) to close with sufficient sealing force to withstand the internal pressure of the LC mobile phase system. Concurrently, a confirming signal is passed to the LC mobile phase controller to commence an interface action.

Referring again to the dual camera systems of the invention for taking front side and backside images of the sample slide (111). The dual cameras of the present system(s) capture their respective positioned images of the sample slides (111). Data from the captured images is sent to software and logic components of the invention. The software and logic utilize the various image data parameters, along with other parameters and data, to determine an ideal or desired punch location (i.e., a best punch location) of the imaged sample from which to obtain (punch) a portion thereof for subsequent downstream processing and/or analysis. The other parameters and data that the software and logic may utilize in determining the desired punch location may be input variables including, but not limited to, properties and characteristics of the absorbed sample (e.g., flow rate, viscosity, color, hue, brilliance, etc.), properties and characteristics of the filtration media (e.g., pore size, thickness, composition, etc.), or even combinations thereof.

While images are captured in pixel data, the software and logic of the invention converts such data for easier use and interpretation thereof. That is images are captured in pixel data, including the area of the captured sample image being captured in pixel area data. Pixel area is a function of the focal length of the camera system used for the image. As such, each of the dual cameras may be calibrated using a square piece of aluminum machined to measure exactly 1.000 inch by 1.000 inch. Using this calibrated measure, along with the pixel area data of each image, the software and logic converts the pixel data into area measured in square inches (i.e., in$^2$). The software and logic may even further convert the inches$^2$ measure into an equivalent "diameter" measure for an easier interpretation thereof. As used and defined herein, the term "diameter" is an area measurement, not a length measurement. For instance, a "diameter" of 0.250 inches is easier to relate to than an area of 0.0490 in$^2$. The following equation may be used for such a conversion into "diameter" of the deposited sample:

$$A = \frac{\pi D^2}{4} \text{ or } D = 2\sqrt{A/\pi}.$$

In certain embodiments of the invention, the systems having the dual cameras and software were employed to determine variables that affect the deposition, absorption and pattern effects of blood spots on filtration media slides. In particular, the systems of the invention were implemented to determine how hematocrit values of blood samples affect the deposition, absorption and pattern effects of deposited blood spots for determining a best punch location from such a DBS. Again, this best punch location will depend upon the ultimate end analysis that is to be performed on the punched specimen or desired result thereof.

Figure 19:
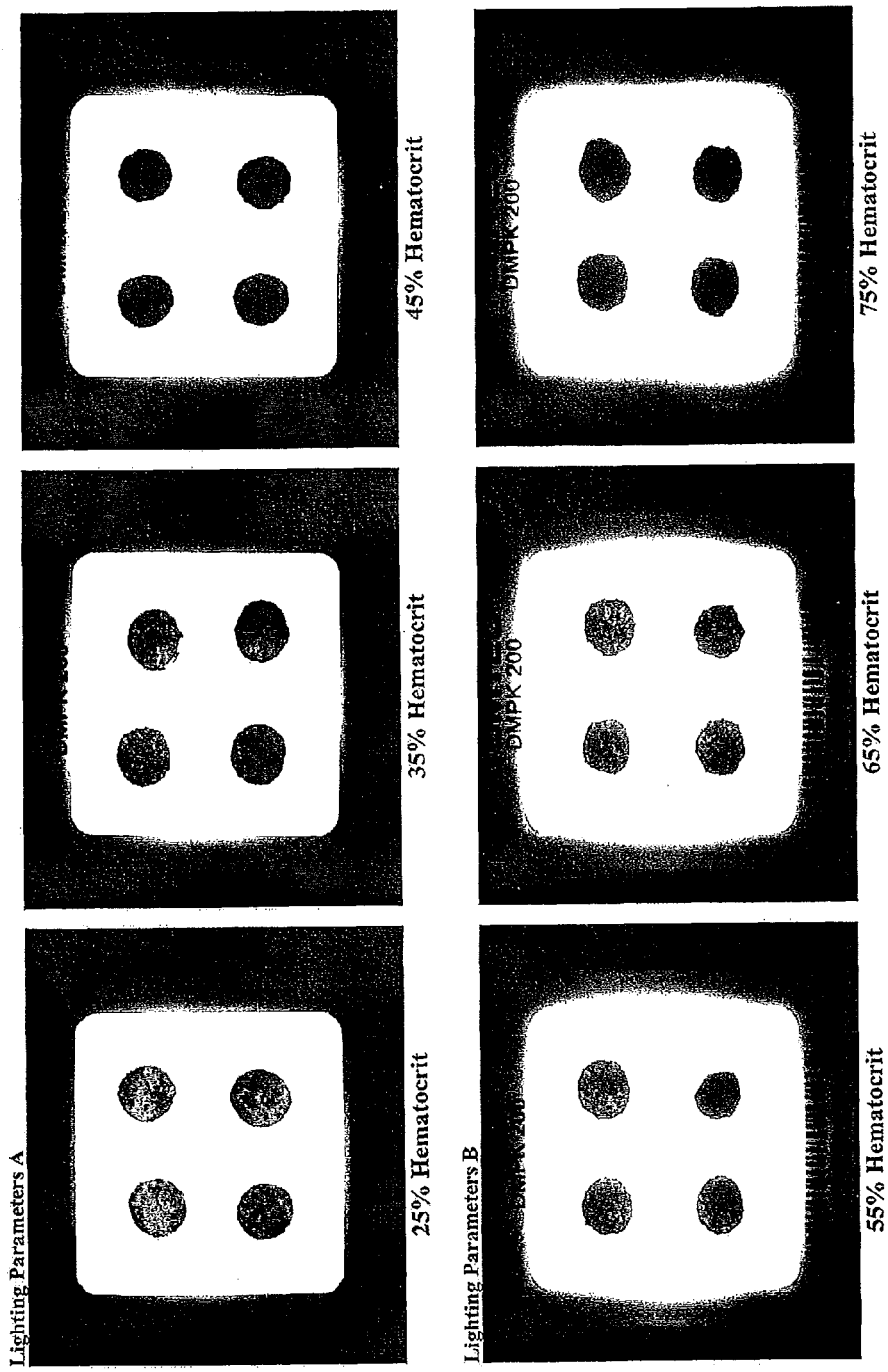
FIG. 19 shows various imaged blood sample spots having different coloring throughout such samples depending upon the amount hematocrit within such samples.

Those DBS samples having higher hematocrit values (i.e., more red blood cells) will be darker in color, and samples having lower hematocrit values will be lighter in color. These darker and lighter image colors can be seen with the naked eye. See, for example, FIG. 19 showing gray areas having lower hematocrit value as compared to black areas having higher hematocrit values. However, much more detailed data relating to such DBS spots can be obtained using the present invention for obtaining the best punch location for each DBS spot.

In one or more embodiments of the invention the dual cameras, software and logic are used to image the front and back sides of the slide, store the image result data, and analyze such image data to determine the front diameter of the DBS sample, the front-to-back differential of the deposited sample, and the color of such sample. All of these parameters are used by the software and logic of the invention to determine the best punch location that includes a desired sampling of the DBS spot that is entirely penetrated with the blood sample. That is, in one or more embodiments, the punched sample may be completely covered with the blood sample throughout its entire thickness, such that, no untreated filtration media material resides within such punched sample.

As discussed above, the front side of the DBS sample is that side of the filtration media that receives the liquid sample. In estimating hematocrit values, the front "diameter" (which again is defined herein as an area measurement, not length) of the DBS sample is obtained by comparing the actual volume of sample deposited onto the media to the area of the spot on the front side. The relationship of hematocrit is consistent with basic fluid mechanics, such that, a low hematocrit blood sample has a lower viscosity than a blood sample having a high hematocrit level.

As shown in the test result data of FIG. 20 the thinner, less viscous blood sample will flow more efficiently over the surface of the absorbent filtration media, as compared to a more viscous, high hematocrit blood sample. If a given volume of liquid sample flows easily over the surface of the filtration media, more of the blood sample will absorb into the media at the front side to generate a larger surface area (i.e., diameter) at such front side, which leaves a lesser volume of sample to soak into and through the absorbent filtration media. A more viscous, high hematocrit blood sample will move across the surface more slowly, leaving a smaller front side "diameter." This slower passage across the filtration media allows more time for the sample to soak into the media, creating the backside spot "diameter."

As such, the present systems may be programmed to detect and identify large front side DBS spot "diameters" as compared to the amount of blood sample deposited onto the media, as corresponding to a blood sample having a low hematocrit value. Conversely, a small front side DBS spot "diameters" as compared to the amount of sample deposited may be identified and correlated with the blood sample having a high hematocrit value.

The invention also captures the backside blood sample image to obtain a back "diameter" of the DBS. For a given liquid volume applied to a specific grade of filtration media there is generally a difference in the size of the front side spot as compared to the size of the backside, which is due to the hematocrit value of the deposited blood sample. Again, a low hematocrit value blood sample has a significantly lower viscosity than a blood sample with a high hematocrit level. Assuming that both the circular areas of the front side image and backside image are on a common central axis, the front side and backside image data are used to calculate an estimated volume contained within the spot area, from the front side of the media to the backside of the media. This may be accomplished using a volume formula of the frustum of a cone.

In the above examples, a specific "spot" was selected for analysis, which was only a portion of the total sample of blood spot area. The camera images provide the front "diameter" and the back "diameter" of the image. The thickness of the filtration media in the slide is known using the equation for the mathematical volume of the frustum of a cone, the volume of the sample spot may be estimated:

$$v = \frac{\pi h}{3}(R_1^2 + R_1 R_2 + R_2^2).$$

The answer is in cubic millimeters, within the conic frustum. The actual sample taken by the punch is also a known cylindrical volume:

$$V = \frac{\pi D^2}{4} \times d$$

Thus, the calculated density of the conical volume may be used to estimate the comparable volume within the punch area, which is the selected volume. Since the blood sample does not flow in a precise conical frustum, this calculation provides a valid estimate of the relationship between the total actual sample volume and the specific percent of that total that was actually analyzed.

In calculating saturation volume area, the differential between the first image and the second image, in combination with a thickness measurement of the sample slide, are used to calculate this measure. This calculation of image volume derived from the camera imaging is then compared to actual volume applied to the filtration media to determine the percent saturation of the applied analyte to the actual punched area taken for analyte recovery by such means as LC-MS/MS. For instance, a blood supply spiked with 4000 ng/mL of an analyte (acetaminophen) was analyzed using the conical frustum method to calculate the mathematical volume of the spot in mm3, which is also μL. This data may vary with hematocrit level, as shown in FIG. 20.

Referring to FIG. 20, as an example, 15 μL was applied to DMPK 200, using 25% hematocrit, the conical volume was 19.36 μL. This shows that the applied volume of 15 μL of liquid analyte only occupied 77% of that area. The punched volume, πD2/4, is then taken for analysis. At least mathematically, that volume only has 77% analyte concentration. Using this mathematical data, with a known starting concentration of 4000 ng/mL, a numerical estimate of the analyte may be obtained that the LC-MS/MS will recover. By collecting sufficient data, using known values, the accuracy of those mathematical calculations with acceptable credibility may be defined. That is, if known starting values of analyte are used, one may predict the amount of recovered analyte with acceptable accuracy.

Another method is available that avoids having to estimate the punched spot volume to the total sample volume. This method analyzes the entire sample spot using a laser to make a scorching mark through the filtration media (i.e., make a mark that defines a delineated area within and cutting through the thickness of the media). For example, a 0.250 inch diameter circle may be isolated leaving holding tabs at 12:00-4:00 and 8:00 o'clock (i.e. 120□ apart). The sample volume is applied to the central area and is retained by the holding tabs. The entire volume of sample within the 0.250 inch circle is removed for analysis by breaking the three holding tabs. The entire sample is then analyzed, such that, estimations are not performed. As discussed above, the x-y coordinates of the receiving 96 well processing plates, slides 1 therein and corresponding delineated sample locations 42 are known or determined by the processing system and equipment so that the whole delineated sample locations 42 (e.g., perforated delineated sample locations 42) are punched for removal and subsequent processing.

Using the principle of basic fluid mechanics, you would expect to see a difference between the front side spot and the backside spot when a liquid is added to the absorbent material due to several factors including, for instance, media thickness, volume of liquid applied, viscosity of the liquid, etc. By changing the volume of the blood applied to the front side of the absorbent filtration media, combined with changing the absorbency of the media, parameters with which to differentiate the front spot "diameter" and the backside spot "diameter" are provided. This provides a means of measuring the flow characteristics of a blood supply that is related to the hematocrit of the applied sample.

There are some other parameters that will affect this relationship, and they must be controlled to minimize variations in the final result. The blood must be uniformly dispensed in one specific location. Gravity should be the only force moving the liquid down into the filtration media. The volume of blood applied must be controlled. To the extent that these outside variables are controlled, will have an effect on the accuracy of the results. For instance variables such as manual pipetting of samples onto the media may introduce human error into the end results. This may be avoided by implementing the automated slide processing and handling aspects of the invention.

Another distinguishing marker for hematocrit is color. A blood sample with a low hematocrit has a much brighter red color than a sample with a high hematocrit. This is obvious to the human eye. However, it is even more distinguishable to a sensitive camera system, particularly when the lighting and camera controls of gain, hue, brilliance, etc. can be controlled for the specific observation conditions. The color variations observed and detected by the present camera optical systems across the DBS sample spot may have a direct relationship and correlation to the quality of the end-results. For example, for some analyses the darker areas (higher hematocrit values) may produce the best results, while in other analyses lighter areas (lower hematocrit values) might produce the best results.

By adjusting various camera processing parameters, the camera optical system is able to obtain more imaging detail as compared to the naked eye. From a logical viewpoint, the color of the blood spot may vary with volume. However, that parameter is the easiest to control. FIG. 19 shows color images (shown in gray scale) of six different hematocrit values at two different lighting parameters. At lighting parameters A, the naked eye is able to view color differences at the hematocrit levels of 25% and 35%. However, the 45% hematocrit is difficult to observe color differences. By adjusting the lighting parameters to parameters B the naked eye is now able to observe color differences at 55% hematocrit and 65% hematocrit, however, the 75% hematocrit is difficult to see.

The dual camera systems of the invention provide for increased control of the various imaging parameters including, but not limited to, intensity, hue, brilliance, and combinations thereof. As such the images captured by the cameras include much more detailed data of the blood spot than can be seen or detected by the naked eye. This detailed camera imaging data is stored and used by the software and logic of the invention for determining a best punch location.

System software and logic implement all this stored data (i.e., front "diameter" data of the DBS sample, front-to-back differential data of the deposited sample, and color data of such sample) to determine a best punch location of the given sample spot. Again, this best punch location is dependent upon the ultimate end goal or use to the punched portion of the sample spot (e.g., analyte recovery from the punched sample spot portion). The present systems may be fully automated, and as such, calibration and/or preset parameters and data may need to be input and stored within the system logic in order to make such a determination. This is accomplished by a system closed loop feedback process or training period.

To achieve the fully automated systems of the invention, the instrumentation of the system must be programmed, or given guidelines and parameters, for detecting specific spots or locations (i.e., best punch locations) within the sample area to punch for downstream processing. In doing so, an end-user or operator may view and select a number of front side and backside imaged sample spots for punching and analysis to determine which of such punched locations provide test results that fall within a predefined set of parameters for such analysis.

For instance, an operator may select one or more areas of interest from the front side and backside of the slides. The dual camera systems then image these locations and data in relation to said locations are stored. Test samples may be run on these areas of interest to determine whether they provide desired results, or results that fall within a predefined range of acceptable parameters. The test run(s) results are stored within the logic of the present systems (i.e., within a database) for programming the present systems for future runs in locating and obtaining other sample spots that meet or exceed these stored parameters.

After these parameters have been stored within the system logic, and it is determined that acceptable runs are being performed with such parameters, the closed loop feedback process may be ended. The present systems are then fully automated for subsequent runs that simply look for specific input parameters to select the optimum point (i.e., best punch location(s)) to punch for a specific sample on a filtration media slide. These runs may be performed on single, individual slides, or alternatively, batches of slides.

Examples implementing the systems and methods of the invention were performed to determine how hematocrit values of blood samples and how they affect the deposition, absorption and pattern effects of such deposited blood spots. Participants deposited blood samples on three different grades of filtration media to provide a variety of DBS slides for analysis thereof in accordance with the invention. These grades of filtration media included DMPK 200 (0.016 inches thick), DMPK 300 (0.026 inches thick) and DMPK 400 (0.032 inches thick), all of Tomtec.

One aspect of the testing was to determine how hematocrit of the incoming DBS slides affected the absorption of the deposited samples, and in turn, determining a best location for punching a portion of such deposited samples for further processing. Pooled blood samples having 6 different hematocrit values were evaluated, and in particular, hematocrit values of 25%, 35%, 45%, 55%, 65%, and 75%.

Samples were deposited onto the filtration media using a manual pipettor and Aqua Caps. The manual pipettor has the potential of injecting the liquid stream into the media. This can either be due to the rate of dispense, or the use of the second stop, blow out feature. The Aqua Cap is a capillary tube with a calibrated plug. In essence, it is a positive displacement pipettor that is calibrated to contain, as well as to deliver. It is filled by capillary action and dispensed by inserting a plunger to expel the plug. It is less susceptible to injecting the contained liquid into the filtration media. For the study, the Aqua Cap was used as a second control on the method of sample dispensing.

In the study three volumes 15 µL, 25 µL, and 40 µL of the different hematocrit value containing samples were deposited (alternately using manual pipettor and Aqua Cap) onto the different grades of filtration media; DMPK 200, DMPK 300, and DMPK 400. The dried blood sample (DBS) slides were then processed using the dual camera system and methods of the invention. That is, a first camera system having its own lighting captured images from a front side of each slide, while a second camera system having its own lighting captured the image from the backside of such slide.

Figure 21:
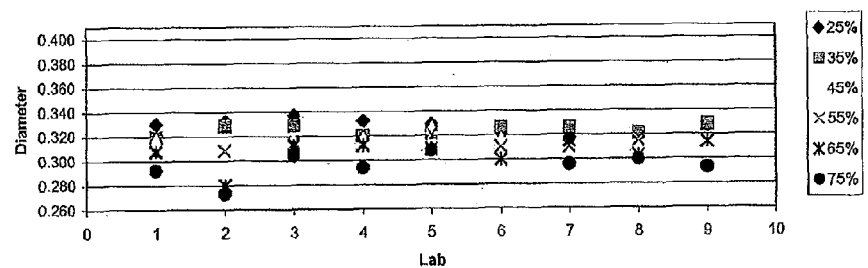
FIGS. 21-22 show test results performed using embodiments of the present methods and systems.
Figure 21:
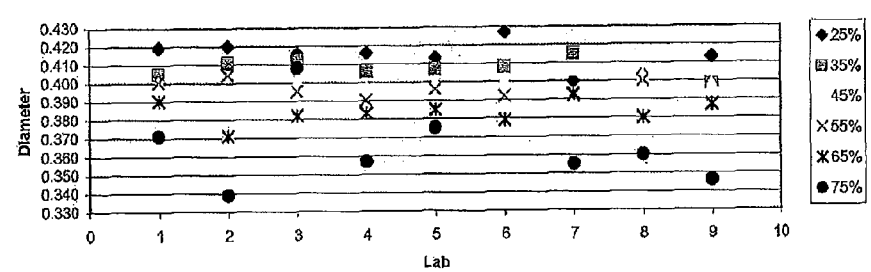
Figure 21:
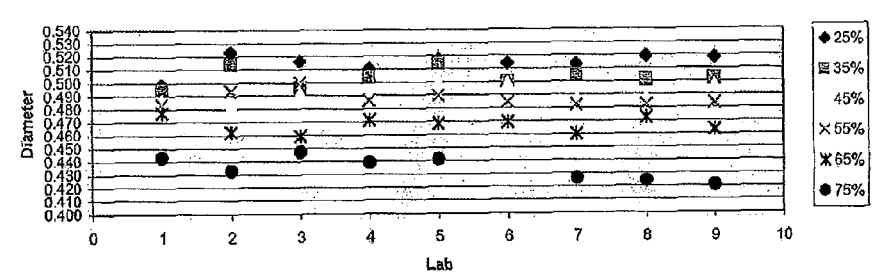

These studies found that the higher the hematocrit levels residing in blood samples, such samples were less spread out over the front side of the filtration media. That is, they had a smaller "diameter" (area) as compared to the less viscous lower hematocrit value blood samples. Likewise, the lower hematocrit value blood samples were spread more easily and were larger in "diameter" (area) across the front side filtration media surface. See, for example, the front "diameter" results of hematocrit value detections for various volumes of differing hematocrit level blood samples deposited by Aqua Cap onto DMPK 200 (0.016 inches thick) filtration media slides as shown in FIG. 21.

Figure 22:
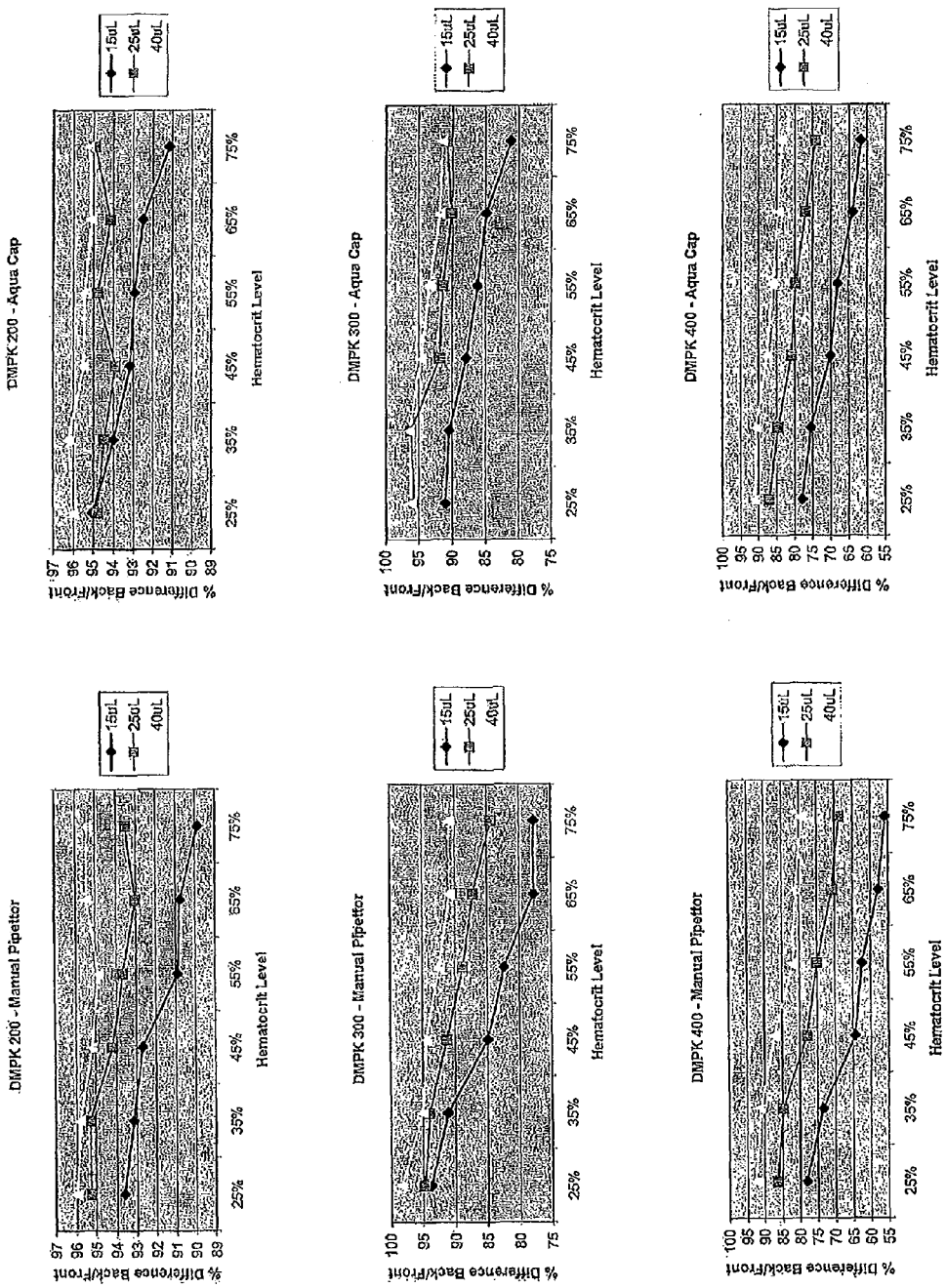

The FIG. 22 results of the "diameter" percent differences from the front side of the media to the backside of the media also show that the greater the volume of sample deposited onto the media, the greater the difference between the front and backside "diameters" of the DBS. These results also show that the smaller the volume of deposited blood of the differing hematocrit level blood samples, the greater the variation between the front side and backside "diameters."

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of utilizing a specimen collection slide comprising:
   providing a specimen collection slide comprising,
      top and bottom rigid layers respectively having first and second central openings;
      a middle rigid layer residing directly between and contacting both said top and bottom rigid layers, the middle rigid layer having a third central opening larger than said first and second central openings;
      a single filtration media layer residing within the third central opening of the middle layer and between said top and bottom rigid layers whereby portions of said filtration media layer contact said top and bottom rigid layers for securing said single filtration media layer there-between, wherein no other filtration media layers reside between the top and bottom rigid layers;

a plurality of predefined delineated locations traversing through the single filtration media layer each indicating locations where one or more samples are to be deposited, a plurality of delineated location unique identifiers residing on the filtration media layer adjacent to the plurality of predefined delineated locations, each said delineated location unique identifier identifying and distinguishing different ones of said predefined delineated locations from one another for sample recall, whereby the top, middle, and bottom rigid layers have substantially same external dimensions, and are securely attached together in a stack without damaging the filtration media to provide the specimen collection slide with a thickness sufficient for handling, the single filtration media layer residing within the middle rigid layer not contacting any other adjacent filtration media;

depositing through at least one of said first and second central openings at least one or more samples onto the single filtration media within the one or more plurality of predefined delineated locations;

allowing the deposited at least one or more samples to dry on the one or more plurality of predefined delineated locations of the filtration media;

identifying at least one of said plurality of predefined delineated locations using said plurality of delineated location unique identifiers; and removing the identified at least one of said plurality of predefined delineated locations containing said dried sample by access through at least one of said first and second central openings for an analytical testing procedure.

2. The method of claim 1 wherein the plurality of predefined delineated locations each comprise a plurality of cut out perforations traversing through the filtration media layer that provide a physical barrier to retain the deposited sample within each said predefined delineated location.

3. The method of claim 2 wherein said plurality of cut out perforations are formed in the filtration media layer using a laser, said laser providing the ability to alter size, location and number of delineated sample locations within the filtration media.

4. The method of claim 2 further including depositing a known volume of said one or more samples onto each of said one or more plurality of predefined delineated locations, whereby said physical barrier retains said known volume of sample within each said predefined delineated locations, subsequently removing said at least one of said plurality of predefined delineated locations containing said dried sample thereby removing said known volume of said sample for the analytical testing procedure.

5. The method of claim 1 further including a primary unique identifier on each said specimen collection slide for distinguishing the specimen collection slide from other specimen collection slides, said primary unique identifier residing on said top or bottom rigid layer.

6. The method of claim 5 wherein together said primary unique identifier and said plurality of delineated location unique identifiers enable both accurate sample identification for said sample deposited within each said plurality of predefined delineated locations and subsequent recall of said specimen collection slide for accurate processing of any remaining ones of said plurality of predefined delineated locations retaining said sample.

7. The method of claim 5 wherein a number of different one or more sample specimens are deposited onto a single specimen collection slide, whereby together said primary unique identifier in combination with said plurality of delineated location unique identifiers enable each of said different sample specimens to be uniquely identified from one another and removed from said single specimen collection slide.

8. The method of claim 1 wherein the top, bottom and middle rigid layers comprise a rigid plastic material, wherein the thickness of the specimen collection slide is sufficient for automated handling.

9. The method of claim 1 wherein the one or more samples is selected from the group consisting of biological samples, chemical samples, or combinations thereof.

10. The method of claim 1 further including stacking one or more specimen collection slides over each other, whereby a second specimen collection slide is provided over said specimen collection slide such that a thickness of each rigid layer of said specimen collection slides provides a height and an empty cavity between adjacent filtration media layers of said specimen collection slides to prevent contact between said adjacent filtration media layers and avoid cross contamination of specimen samples residing on adjacent specimen collection slides.

11. A specimen collection slide comprising:

top and bottom rigid layers respectively having first and second central openings;

a middle rigid layer residing directly between and contacting, both said top and bottom rigid layers, the middle rigid layer having a third central opening larger than said first and second central openings;

a single filtration media layer residing within the third central opening of the middle layer and between said top and bottom rigid layers whereby portions of said filtration media layer contact said top and bottom rigid layers for securing said filtration media layer therebetween, wherein no other filtration media layers reside between the top and bottom rigid layers;

a plurality of predefined delineated locations traversing through the filtration media layer each indicating locations where one or more samples are to be deposited, said plurality of predefined delineated locations are accessible from said first and second central openings in the top and bottom rigid layers for deposition of the one or more samples and for removal of one or more of said plurality of predefined delineated locations having said deposited sample, a plurality of delineated location unique identifiers residing on the filtration media layer adjacent to the plurality of predefined delineated locations, each said delineated location unique identifier identifying and distinguishing different ones of said predefined delineated locations from one another for subsequent sample processing and recalling procedures, whereby the top, middle, and bottom rigid layers have substantially same external dimensions, and are securely attached together in a stack without damaging the filtration media to provide the specimen collection slide with a thickness sufficient for handling, the filtration media layer residing within the middle rigid layer not contacting any other adjacent filtration media.

12. The specimen collection slide of claim 11 further including a primary unique identifier on each said specimen collection slide for distinguishing the specimen collection slide from other specimen collection slides.

13. The specimen collection slide of claim 12 wherein the primary unique identifier is a universally distinct unique identifier that is permanently provided on at least one of the top and bottom rigid layers to maintain sample identification consistency for positive sample identification from source to discard.

14. The specimen collection slide of claim 12 wherein together said primary unique identifier and said plurality of delineated location unique identifiers enable both accurate sample identification for said sample deposited within each said plurality of predefined delineated locations and subsequent recall of said specimen collection slide for accurate processing of any remaining ones of said plurality of predefined delineated locations retaining said sample.

15. The specimen collection slide of claim 12 wherein a number of different sample specimens are deposited onto a single specimen collection slide, whereby together said primary unique identifier in combination with said plurality of delineated location unique identifiers enable each of said different sample specimens to be uniquely identified from one another and removed from said single specimen collection slide.

16. The specimen collection slide of claim 11 wherein the first, second and third rigid layers comprise a plastic material.

17. The specimen collection slide of claim 11 wherein the plurality of predefined delineated locations each comprise a plurality of cut out perforations traversing through the filtration media layer that identify where one or more samples are to be deposited onto the filtration media and provide a physical barrier to retain the deposited sample within each said predefined delineated location.

18. The specimen collection slide of claim 16 wherein the physical barrier of the plurality of predefined delineated locations enables a known volume of said samples to be deposited only within each of said one or more plurality of predefined delineated locations, and subsequently removed to obtain said known volume of said sample for the analytical testing procedure.

* * * * *

UNITED STATES PATENT AND TRADEMARK OFFICE
CERTIFICATE OF CORRECTION

PATENT NO. : 9,903,798 B1
APPLICATION NO. : 15/337164
DATED : February 27, 2018
INVENTOR(S) : Thomas W. Astle It is certified that error appears in the above-identified patent and that said Letters Patent is hereby corrected as shown below:

In the Specification

In Column 9, Line 38, delete "thy" and substitute therefore -- dry --.

Signed and Sealed this
Twentieth Day of November, 2018

Andrei Iancu
*Director of the United States Patent and Trademark Office*